US012702302B2

(12) United States Patent
Wang et al.

(10) Patent No.: US 12,702,302 B2
(45) Date of Patent: Aug. 11, 2026

(54) STRAIN-INSENSITIVE SOFT PRESSURE SENSOR AND METHOD OF MEASURING PRESSURE

(71) Applicant: The University of Chicago, Chicago, IL (US)

(72) Inventors: Sihong Wang, Chicago, IL (US); Qi Su, Chicago, IL (US); Yang Li, Chicago, IL (US)

(73) Assignee: THE UNIVERSITY OF CHICAGO, Chicago, IL (US)

( * ) Notice: Subject to any disclaimer, the term of this patent is extended or adjusted under 35 U.S.C. 154(b) by 314 days.

(21) Appl. No.: 18/290,499

(22) PCT Filed: May 9, 2022

(86) PCT No.: PCT/US2022/028316

§ 371 (c)(1),
(2) Date: Nov. 14, 2023

(87) PCT Pub. No.: WO2022/250939

PCT Pub. Date: Dec. 1, 2022

(65) Prior Publication Data

US 2024/0255362 A1 Aug. 1, 2024

Related U.S. Application Data

(60) Provisional application No. 63/193,819, filed on May 27, 2021.

(51) Int. Cl.
*G01L 1/14* (2006.01)
*A61B 5/00* (2006.01)
*G01L 5/00* (2006.01)

(52) U.S. Cl.
CPC .......... *A61B 5/0053* (2013.01); *A61B 5/6826* (2013.01); *A61B 5/6843* (2013.01);
(Continued)

(58) Field of Classification Search
CPC . G01L 1/16; G01L 1/146; G01L 1/142; G01L 1/14
See application file for complete search history.

(56) References Cited

U.S. PATENT DOCUMENTS 4,056,742 A * 11/1977 Tibbetts ............... H10N 30/204 310/357
4,258,100 A * 3/1981 Fujitani .................. B32B 25/10 219/91.21

(Continued)

FOREIGN PATENT DOCUMENTS

CN 110346079 A 10/2019

OTHER PUBLICATIONS

Araki, et al., "Wireless Monitoring Using a Stretchable and Transparent Sensor Sheet Containing Metal Nanowires," Advanced Materials, vol. 32, No. 15 (2020), pp. 1902684.

(Continued)

*Primary Examiner* — Tran M. Tran
(74) *Attorney, Agent, or Firm* — Crowell & Moring LLP

(57) ABSTRACT

A soft pressure sensor comprises a stretchable top electrode, a stretchable bottom electrode, and an array of peaked structures between the stretchable top and bottom electrodes. The peaked structures comprise protruding regions of a continuous film conformally overlying an array of stiffening electrodes on the stretchable bottom electrode, where a tip of each protruding region is in contact with the stretchable top electrode and a base of each stiffening electrode is in contact with the stretchable bottom electrode. The soft pressure sensor includes one or more spacers extending between and bonded to the stretchable top electrode and the continuous film on the stretchable bottom electrode, where each of the one or more spacers is positioned outside the array of peaked structures. A capacitance (Continued)

measured by the soft pressure sensor is substantially invariant under in-plane stretching and/or bending.

14 Claims, 26 Drawing Sheets

(52) U.S. Cl.
CPC ........ *G01L 1/14* (2013.01); *A61B 2562/0247* (2013.01); *A61B 2562/12* (2013.01)

(56) References Cited

U.S. PATENT DOCUMENTS 4,384,394 A * 5/1983 Lemonon ............. H10N 30/308 264/479
4,852,443 A * 8/1989 Duncan .................. G10H 3/146 84/DIG. 12
4,866,412 A * 9/1989 Rzepczynski ....... G06F 3/04144 338/114
5,425,275 A * 6/1995 Lockshaw ............... G01L 1/142 324/519
5,642,015 A * 6/1997 Whitehead ............. H02N 1/006 310/309
5,755,909 A * 5/1998 Gailus .................... H10N 30/87 29/25.35
5,841,143 A * 11/1998 Tuma ................... G01N 21/648 250/459.1
6,337,173 B2 * 1/2002 Jen .................... H01L 21/76213 430/394
6,606,540 B1 * 8/2003 Gross ........................ G01L 1/24 701/28
7,104,146 B2 * 9/2006 Benslimane ............. G01D 5/24 73/862.626
7,178,405 B2 * 2/2007 Sato ........................ G01L 1/205 73/818
7,573,064 B2 * 8/2009 Benslimane ......... H10N 30/206 257/306
7,732,999 B2 * 6/2010 Clausen ............... H10N 30/098 310/369
7,791,248 B2 * 9/2010 Cross ................... H10N 30/852 310/365
8,033,189 B2 * 10/2011 Hayakawa ............. B25J 13/084 901/46
8,393,229 B2 * 3/2013 Tao .......................... A43B 3/44 73/862.632
8,613,231 B2 * 12/2013 Muroyama ............. G01L 5/228 73/862
8,891,222 B2 * 11/2014 Benslimane ........... H04R 19/00 361/278
9,324,733 B2 * 4/2016 Rogers ................. H10D 48/345
9,752,940 B2 * 9/2017 Ogura ..................... G01L 1/142
9,785,296 B2 * 10/2017 Lee ....................... G06F 3/0445
9,816,882 B2 * 11/2017 Zhang .................... A61B 34/30
9,851,271 B2 * 12/2017 Koo ....................... B25J 13/084
9,904,395 B2 * 2/2018 Ogura ..................... G01L 1/144
9,945,739 B2 * 4/2018 Jeon .......................... G01L 1/14
9,981,420 B2 * 5/2018 Benaissa ................... B32B 3/28
10,037,098 B2 * 7/2018 Bao ..................... G06F 3/04144
10,126,191 B2 * 11/2018 Li ......................... G01L 9/0044
10,485,430 B2 * 11/2019 Afzali-Ardakani ......................... A61B 5/0205
10,718,676 B2 * 7/2020 Chen .................... H10N 70/826
10,722,174 B2 * 7/2020 Pang .................... A61B 5/6833
10,860,129 B2 * 12/2020 Lim .................. H01L 21/02617
10,933,877 B2 * 3/2021 Lussier .................. B62D 55/12
10,978,595 B2 * 4/2021 Baek ....................... G01L 1/005
11,025,251 B2 * 6/2021 Kraemer .............. H03K 17/964
11,073,434 B2 * 7/2021 Cha ........................ H10N 30/02
11,216,103 B2 * 1/2022 Zhang ............... G02F 1/133602
11,406,270 B2 * 8/2022 Afzali-Ardakani ......................... A61B 5/6843
11,594,672 B2 * 2/2023 Malhotra ............. G02B 5/1847
11,614,377 B2 * 3/2023 Park ...................... G01L 9/0051 73/724
11,839,453 B2 * 12/2023 Khine .................... A61B 5/022
12,044,584 B2 * 7/2024 Guo ........................ G01L 5/165
12,092,536 B1 * 9/2024 Wang ........................ G01L 1/18
12,196,626 B2 * 1/2025 Vardoulis ................. A61B 5/00
12,259,287 B2 * 3/2025 Tee ........................... G01L 1/18
12,292,346 B2 * 5/2025 Wang ................ A61B 5/02108
12,364,089 B2 * 7/2025 Khademhosseini .... G01L 1/005
12,392,673 B2 * 8/2025 Tee ......................... G01L 1/205
12,399,071 B2 * 8/2025 Vanfleteren ............. G01L 1/146
12,422,315 B2 * 9/2025 Aihara ...................... G01L 1/14
12,492,955 B2 * 12/2025 Beker ..................... G01L 5/228
2004/0012301 A1 * 1/2004 Benslimane ......... H10N 30/206 310/311
2010/0298895 A1 11/2010 Ghaffari et al.
2013/0047747 A1 * 2/2013 Joung ................ G06F 3/04142 73/862.68
2014/0218872 A1 * 8/2014 Park ..................... H05K 1/0283 216/13
2015/0355039 A1 * 12/2015 Duchaine ................ G06F 3/044 428/141
2016/0349134 A1 * 12/2016 Jeon ....................... A61B 34/00
2016/0365198 A1 * 12/2016 Pan ...................... H01G 5/0132
2017/0097315 A1 * 4/2017 Lee .......................... H05K 1/09
2019/0305139 A1 * 10/2019 Baek ....................... G01L 1/005
2020/0149987 A1 * 5/2020 Ahamed ............. B29C 37/0053
2020/0397321 A1 12/2020 Dirksen et al.
2022/0128420 A1 * 4/2022 Tee ...................... A61B 5/0285
2023/0277080 A1 * 9/2023 Khademhosseini ... A61B 5/681 600/547
2025/0027827 A1 * 1/2025 Sonkusale ............ H10K 10/484

OTHER PUBLICATIONS

An, et al., “Transparent and flexible fingerprint sensor array with multiplexed detection of tactile pressure and skin temperature,” Nature Communications, vol. 9, 2458 (2018), pp. 1-10.

Bai, et al., “Stretchable distributed fiber-optic sensors,” Science, vol. 370, No. 6518 (2020), pp. 848-852.

Boutry, et al., “A stretchable and biodegradable strain and pressure sensor for orthopaedic application,” Nature Electronics, vol. 1, No. 5 (2018), pp. 314-321.

Boutry, et al., “Biodegradable and flexible arterial-pulse sensor for the wireless monitoring of blood flow,” Nature Biomedical Engineering, vol. 3 (2019), pp. 47-57.

Cheng, et al., “Stretchable electronic skin based on silver nanowire composite fiber electrodes for sensing pressure, proximity, and multidirectional strain,” Nanoscale, vol. 9 (2017), pp. 3834-3842.

Choi, et al., “Highly conductive, stretchable and biocompatible Ag-Au core-sheath nanowire composite for wearable and impantable bioelectronics,” Nature Nanotechnology, vol. 13, No. 11 (2018), pp. 1048-1056.

Choong, et al., “Highly stretchable resistive pressure sensors using a conductive elastomeric composite on a micropyramid array,” Advanced Materials, vol. 26, No. 21, (2014), pp. 3451-3458.

Dai, et al., “Stretchable transistors and functional circuits for human-integrated electronics,” Nature Electronics, vol. 4, No. 1 (2021), pp. 17-29.

Han et al., “Battery-free, wireless sensors for full-body pressure and temperature mapping,” Science Translational Medicine, vol. 10, No. 435 (2018), eeam4950.

Hassani, et al., “Soft sensors for a sensing-actuation system with high bladder voiding efficiency,” Science Advances, vol. 6, No. 18 (2020), eaba0412.

Hinchet et al., “Transcutaneous ultrasound energy harvesting using capacitive triboelectric technology,” Science, vol. 365, No. 6452 (2019), pp. 491-494.

Hua, et al., “Skin-inspired highly stretchable and conformable matrix networks for multifunctional sensing,” Nature Communications, vol. 9, No. 244 (2018), pp. 1-11.

Hwang, et al., “A transparent stretchable sensor for distinguishable detection of touch and pressure by capacitive and piezoresistive signal transduction,” NPG Asia Materials, vol. 11, (2019), 23.

(56) References Cited

OTHER PUBLICATIONS

Kim, et al., "Stretchable electronics on another level," Nature Electronics, vol. 1, No. 8 (2018), pp. 440-441.
Larson, et al., "Highly stretchable electroluminescent skin for optical signaling and tactile sensing," Science, vol. 351, No. 6277 (2016), pp. 1071-1074.
Lee, et al., "A transparent bending-insensitive pressure sensor," Nature vol. 11, No. 5 (2016), pp. 472-478.
Lee, et al., "Nanomesh pressure sensor for monitoring finger manipulation without sensory interference," Science, vol. 370, No. 6519 (2020), pp. 966-970.
Niu, et al., "A wireless body area sensor network based on stretchable passive tags," Nature Electronics, vol. 2, (2019), pp. 361-368.
O'Brien, et al., "Elastomeric passive transmission for autonomous force-velocity adaptation applied to 3D-printed prosthetics," Science Robotics, vol. 3, No. 23 (2018), eaau5543.
Pan, et al., "A supertough electro-tendon based on spider silk composites," Nature, vol. 11, No. 1332 (2020), pp. 1-9.
Pang, et al., "A flexible and highly sensitive strain-gauge sensor using reversible interlocking of nanofibres," Nature Materials, vol. 11, (2012), pp. 795-801.
Qin, et al., "Highly stretchable and nonvolatile gelatin-supported deep eutectic solvent gel electrolyte-based ionic skins for strain and pressure sensing," Journal of Materials Chemistry C, vol. 7, (2019), pp. 601-608.
Roh, et al., "A solution-processable, omnidirectionally stretchable, and high-pressure-sensitive piezoresistive device," Advanced Materials, vol. 29, No. 42 (2017), 1703004.
Sankar, et al., "Texture Discrimination with a Soft Biomimetic Finger Using a Flexible Neuromorphic Tactile Sensor Array That Provides Sensory Feedback," Soft Robotics, vol. 8, No. 5 (2021), pp. 577-587.
Sarkar and Kundu, "Nonbonding interaction analyses on PVDF/[BMIM][BF4] complex system in gas and solution phase," Journal of Molecular Modeling, vol. 25, 131 (2019), pp. 1-27.
Sugiyama, et al., "An ultraflexible organic differential amplifier for recording electrocardiograms," Nature Electronics, vol. 2, (2019), pp. 351-360.
Wang, et al., "Strain-insensitive intrinsically stretchable transistors and circuits," Nature Electronics, vol. 4, (2021), pp. 143-150.
Wang, et al., "Skin electronics from scalable fabrication of an intrinsically stretchable transistor array," Nature, vol. 555, (2018), pp. 83-88.
Wang, et al., "Gesture recognition using a bioinspired learning architecture that integrates visual data with somatosensory data from stretchable sensors," Nature Electronics, vol. 3, (2020), pp. 563-570.
Wang, et al., "Stretchable fluoroelastomer quasi-solid-state organic electrolyte for high-performance asymmetric flexible supercapacitors," Journal of Materials Chemistry A, vol. 4, No. 38 (2016), pp. 14839-14848.
Yang, et al., "Microstructured Porous Pyramid-Based Ultrahigh Sensitive Pressure Sensor Insensitive to Strain and Temperature," ACS Applied Materials & Interfaces, vol. 11, No. 19 (2019), pp. 19472-19480.
Zhang, et al., "Highly Stretchable and Sensitive Pressure Sensor Array Based on Icicle-Shaped Liquid Metal Film Electrodes," ACS Applied Materials & Interfaces, vol. 12, No. 24 (2020), pp. 27961-27970.
Zhang, et al., "Flexible and self-powered temperature-pressure dual-parameter sensors using microstructure-fram-supported organic thermoelectric materials," Nature Communications, vol. 6, 8356 (2015), pp. 1-10.
International Search Report and Written Opinion issued in International Application No. PCT/US22/28316 dated Aug. 17, 2022, pp. 1-7.

* cited by examiner

STRAIN-INSENSITIVE SOFT PRESSURE SENSOR AND METHOD OF MEASURING PRESSURE

RELATED APPLICATIONS

The present patent document is the U.S. national stage of International Application No. PCT/US2022/028316, which was filed on May 9, 2022, and which claims the benefit of priority under 35 U.S.C. 119(e) to U.S. Provisional Patent Application No. 63/193,819, which was filed on May 27, 2021. Both applications are hereby incorporated by reference in their entirety.

GOVERNMENT LICENSE RIGHTS

This invention was made with government support under grant number 2011854 awarded by the National Science Foundation. The government has certain rights in the invention.

TECHNICAL FIELD

This disclosure relates generally to pressure sensors and more particularly to a stretchable and strain-insensitive soft pressure sensor.

BACKGROUND

In any soft tissue, such as human skin or a soft robotic skin, pressure created through external and internal physical contacts is a primary means to perceive physical interactions and may also carry physiological information regarding health conditions. As such, soft pressure sensors that transduce mechanical stimuli into electrical signals may enable applications ranging from medical implants, wearable health monitoring and prosthetic e-skins, to technologies including artificial intelligence, human-machine interactions and soft robotics. Since the motion of human bodies and soft robots is typically associated with substantial deformation of the skin, tissues and/or organs, it is indispensable to render such soft pressure sensors with comparable stretchability. In other words, there is a need for pressure sensors that can function while conformably attached to surfaces (e.g., skin) under stretching deformation. A key challenge is the significant alteration of quantitative pressure sensing performance when the sensor undergoes stretching deformation, which arises from the inherent coupling of mechanical deformation along different directions of a structure. For example, a longitudinal strain induces normal compression, similar to the deformation from a normal pressure. This coupling can greatly complicate the application of such sensors for quantitative measurements of pressure under varied strain states.

DRAWINGS

In order that the disclosure may be well understood, there will now be described various forms thereof, given by way of example, reference being made to the accompanying drawings, in which:

FIG. 1 provides an exploded-view schematic of an exemplary soft pressure sensor.

Figure 6:
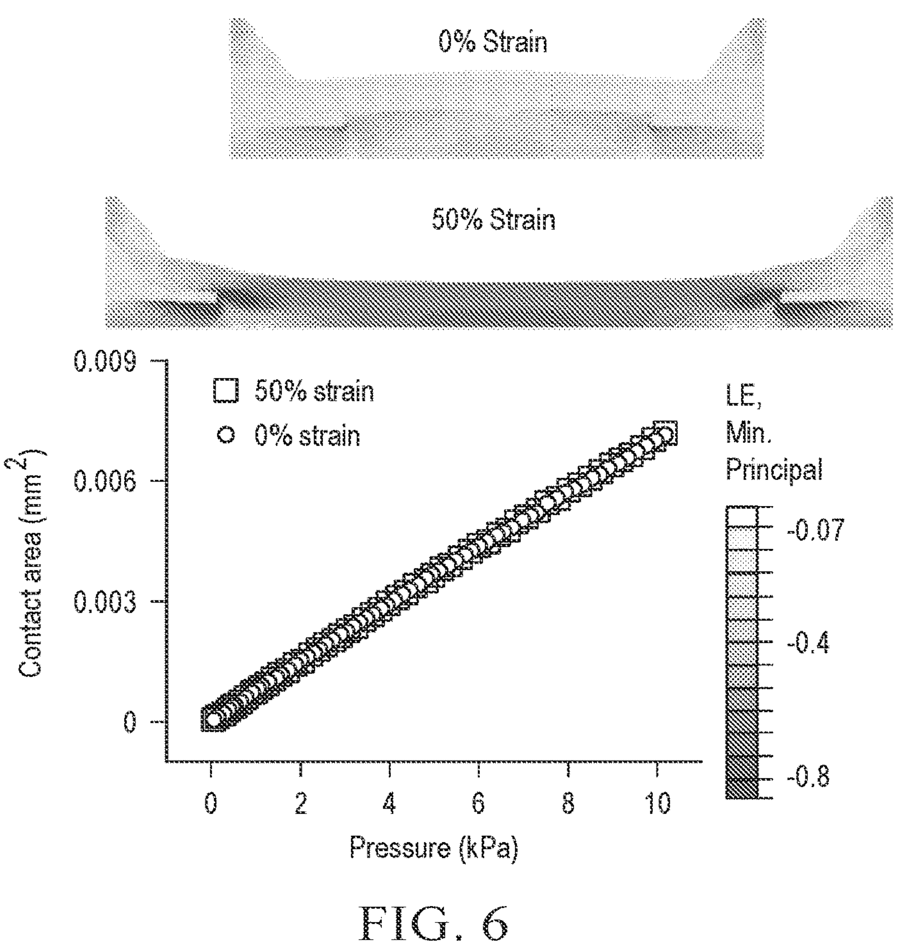

FIG. 6 shows a finite-element simulation (top) of the sensor's pressure-sensing behavior, in particular, the minimum principal logarithmic strain distribution in the dielectric layer under the normal pressure of 10 kPa when there is in-plane strain of 0% and 50% strains, and a plot (bottom) of the increase of the contact area between the pyramid tips and the top electrode surface under the increased pressure, which is proportional to the change of the EDL capacitance.

Figure 7:
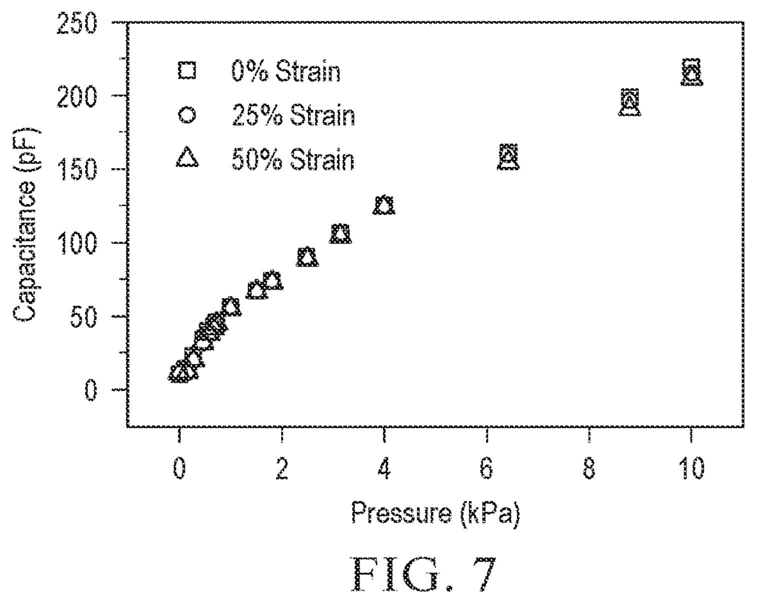

FIG. 7 shows capacitance responses of the sensor at 0%, 25% and 50% strains.

Figure 8:
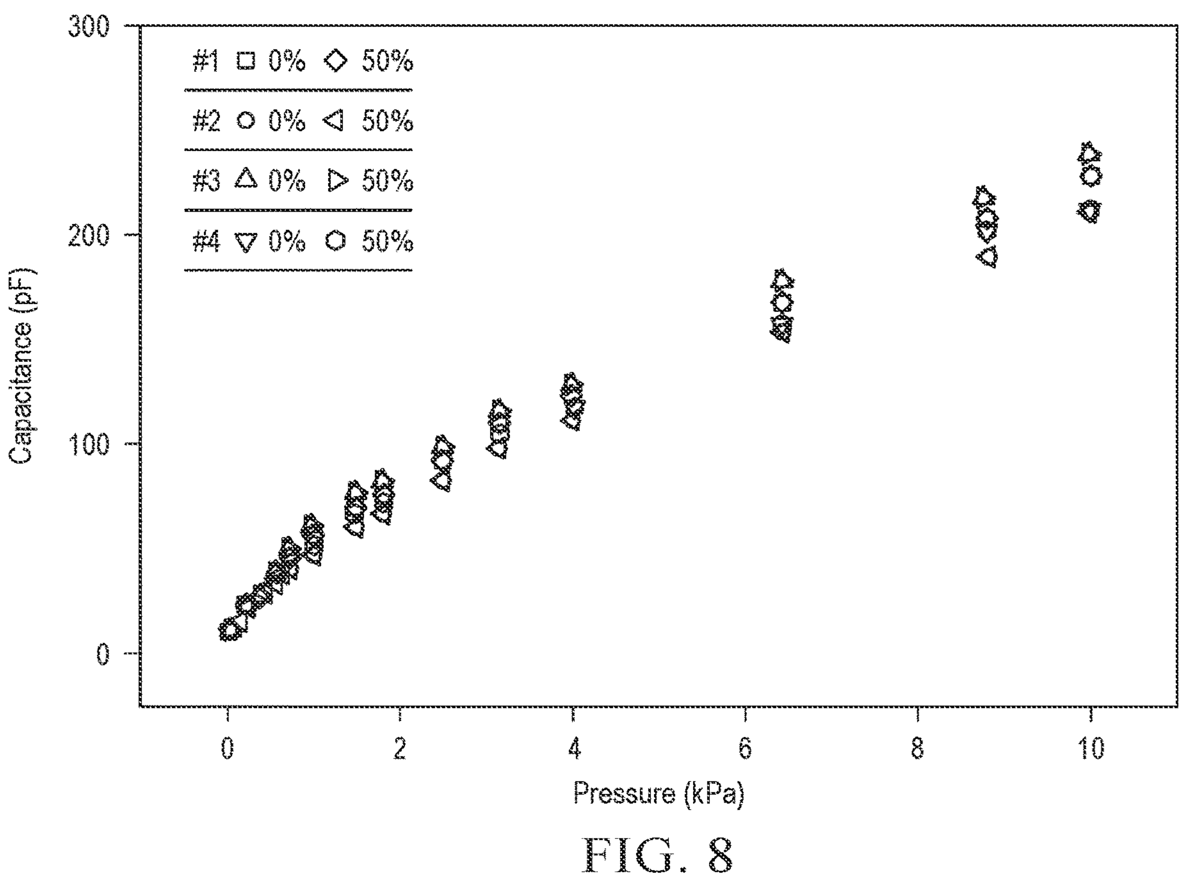

FIG. 8 shows capacitance responses to pressures from four separately fabricated soft pressure sensors when each sensor is at 0% and 50% strains.

Figure 9:
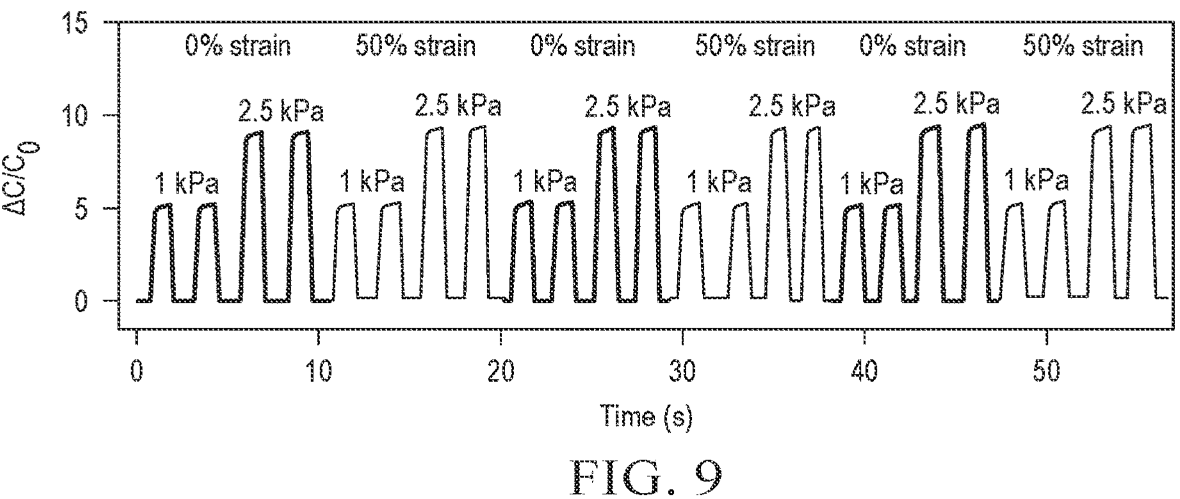

FIG. 9 shows typical performance repeatability of an exemplary soft pressure sensor under repeated pressure loading and repeated stretching cycles between 0% and 50% strains, where Co is the initial capacitance and ΔC is the capacitance change.

Figure 10:
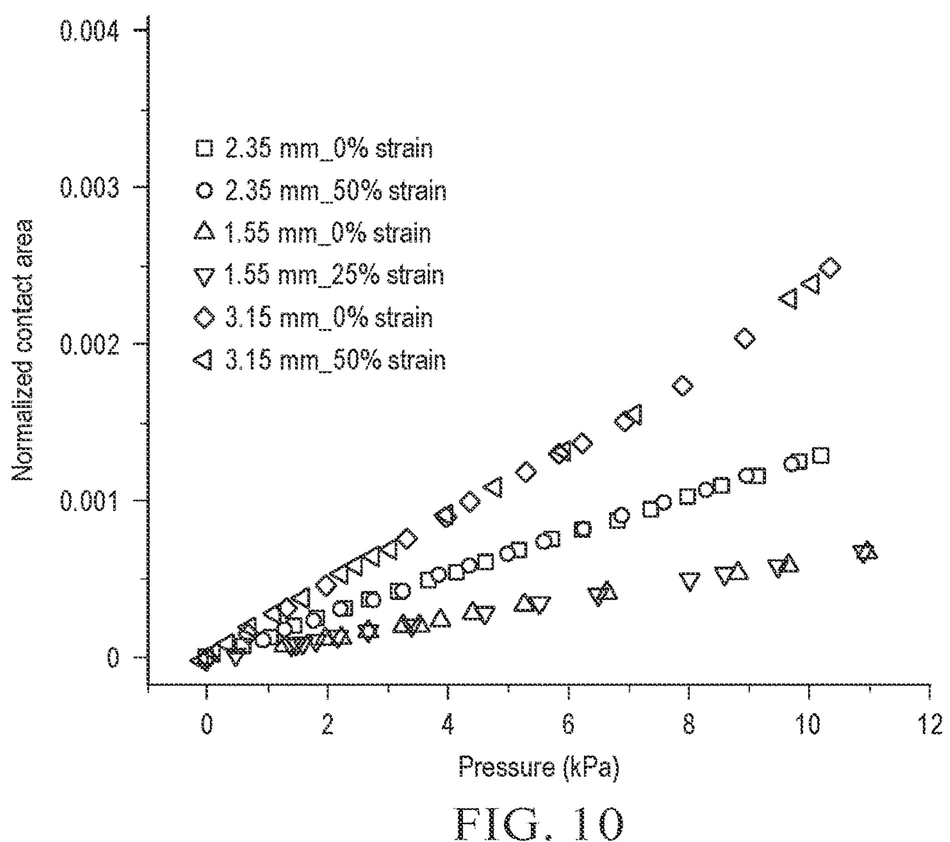

FIG. 10 shows the simulated relationship between contact area and applied pressure for different interspace distances between peaked structures.

Figure 11:
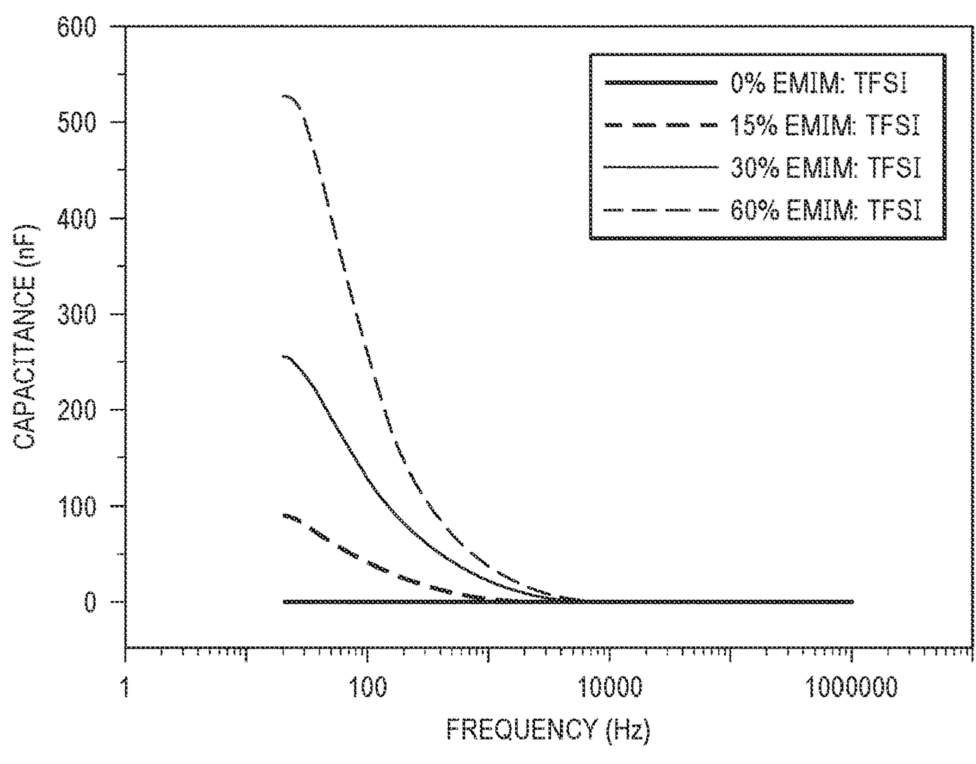

FIG. 11 shows capacitance-frequency relations of continuous films formed using 1% HMDA and variable percentages of ionic liquid (EMIM:TFSI in this example). For testing, the continuous films were sandwiched between two silver nanoparticle paste electrodes of 1 $cm^2$ and the capacitance responses at different frequencies were measured with a LCR meter at 1 Vrms.

Figure 12:
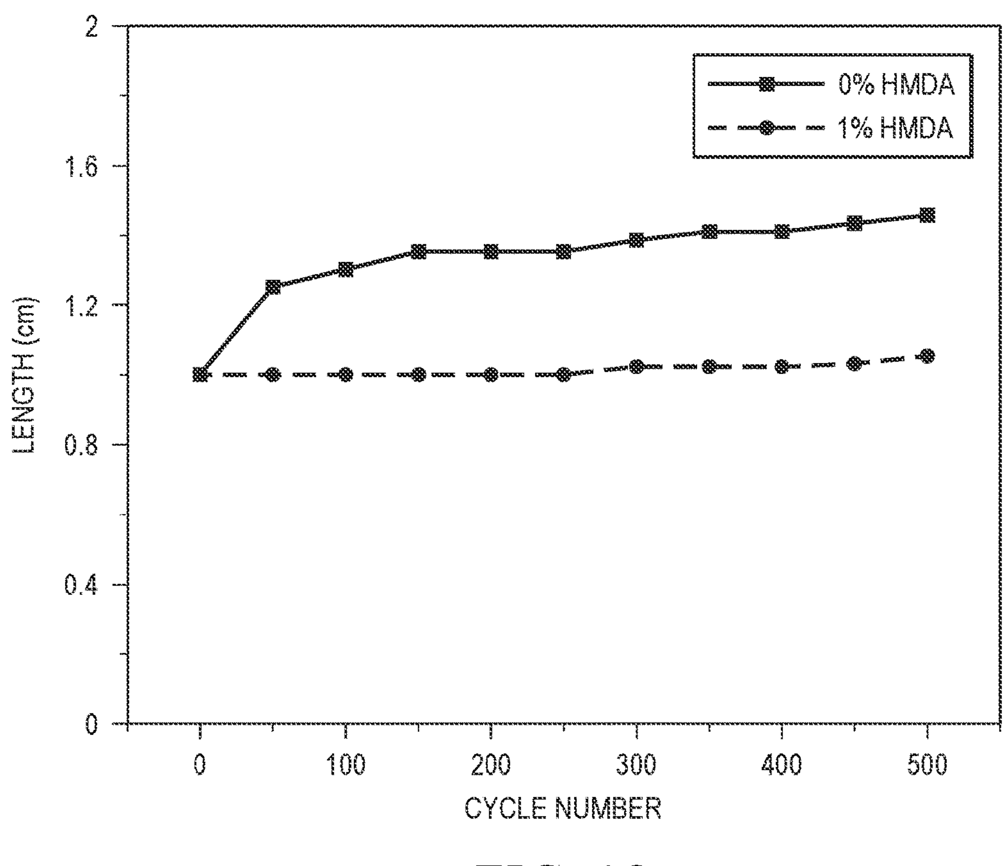

FIG. 12 shows results of fatigue testing of continuous films fabricated using 30% EMIM:TFSI and various percentages (0% and 1%) of HMDA.

Figure 13:
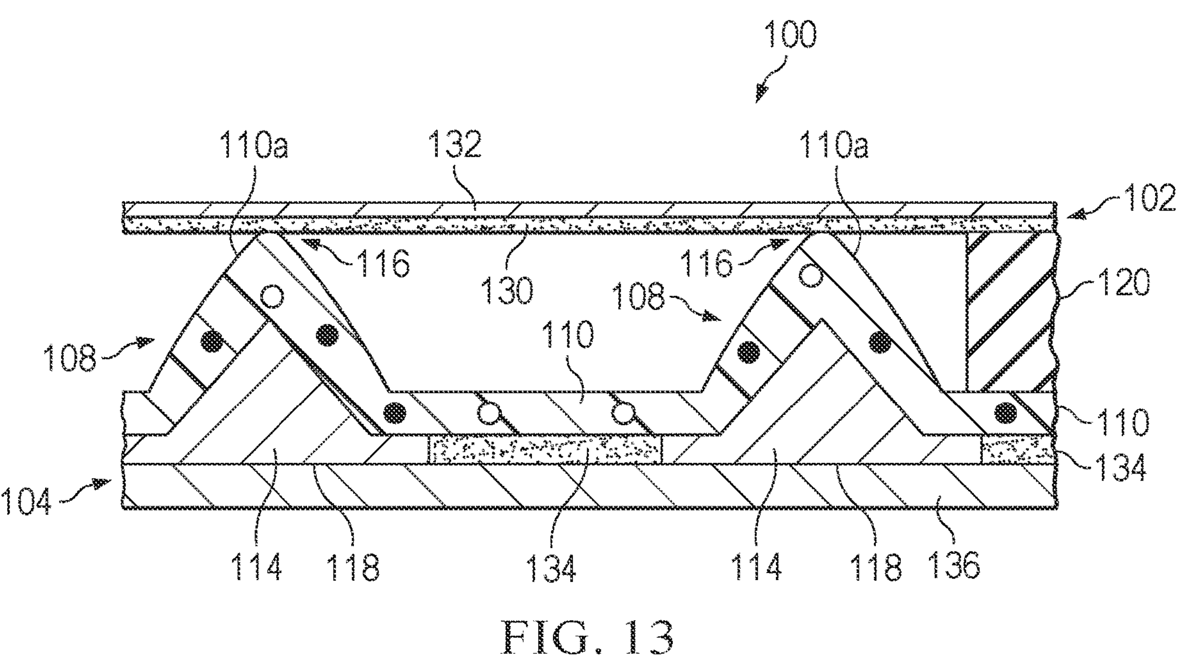

FIG. 13 shows a close-up cross-sectional schematic of part of an exemplary soft pressure sensor.

Figure 14:
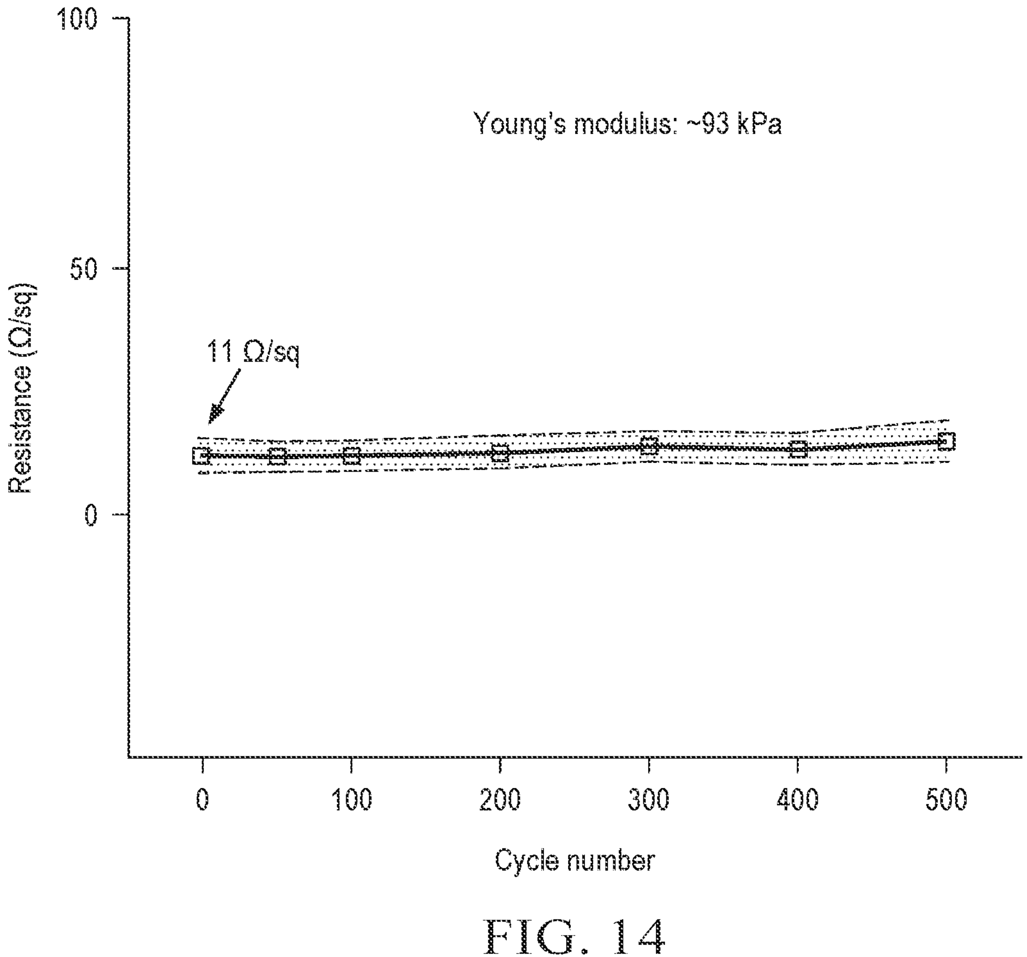

FIG. 14 shows sheet resistance versus cycle for an exemplary stretchable electrode during 500 cycles of repeated stretching to 50% strain.

Figure 15A:
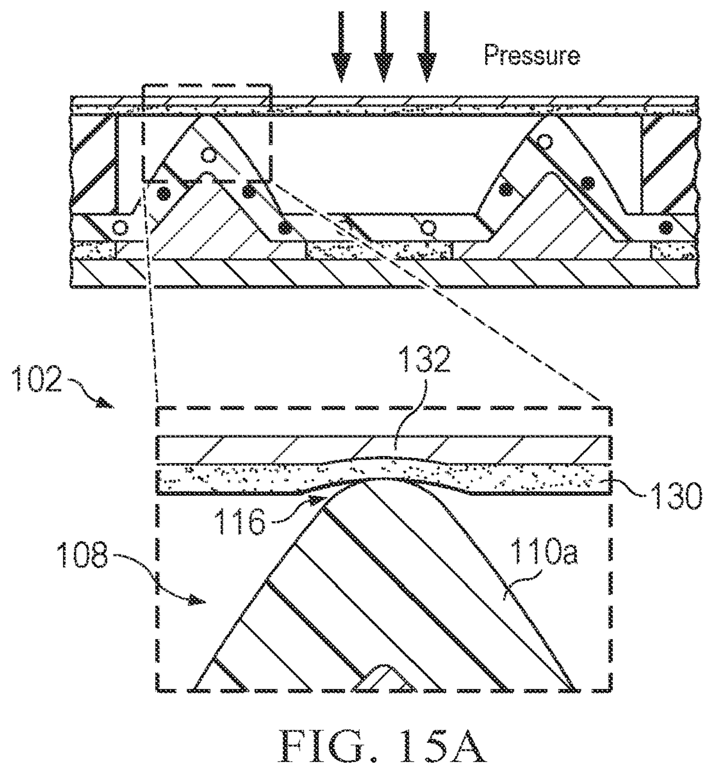

FIG. 15A shows a schematic illustration of what may be described as the "coverage effect" of the stretchable top electrode.

Figure 15B:
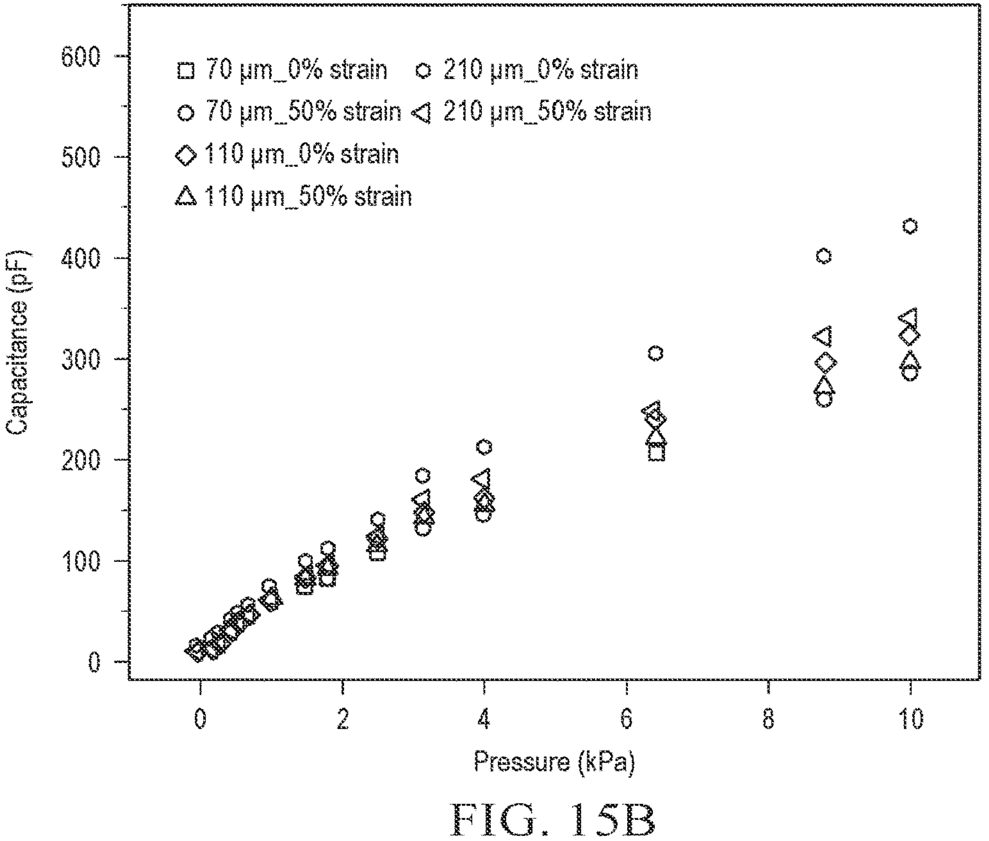

FIG. 15B shows capacitance response of soft pressure sensors including stretchable top electrodes having different elastomeric layer thicknesses.

Figure 16A:
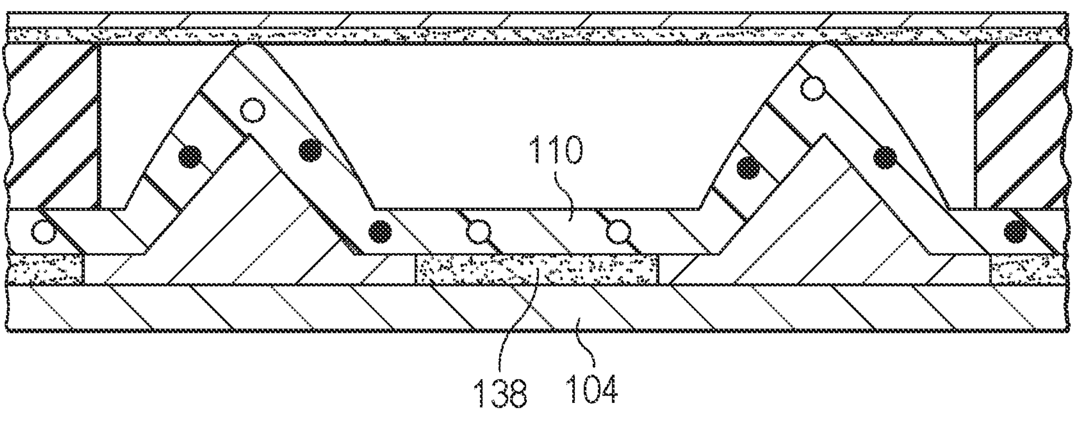
Figure 16B:
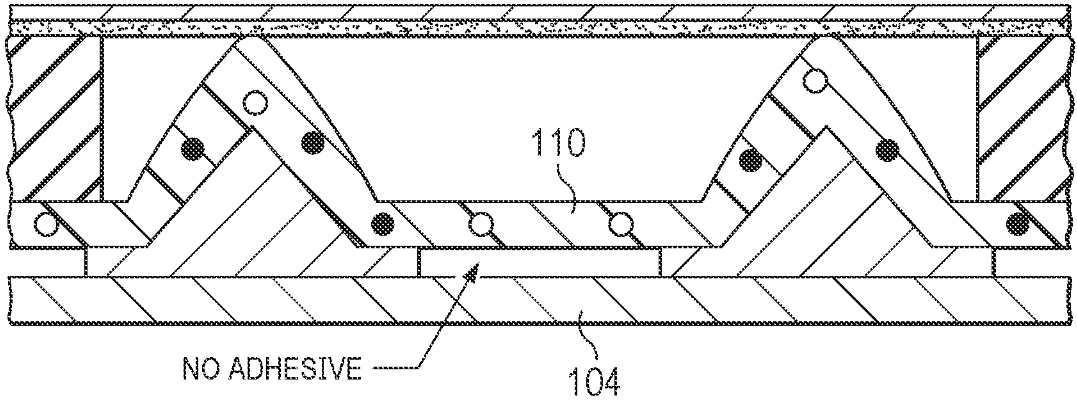

FIGS. 16A and 16B are cross-sectional schematics of part of a soft pressure sensor that includes and does not include, respectively, a conductive adhesive between the continuous film and the stretchable bottom electrode.

Figure 17:
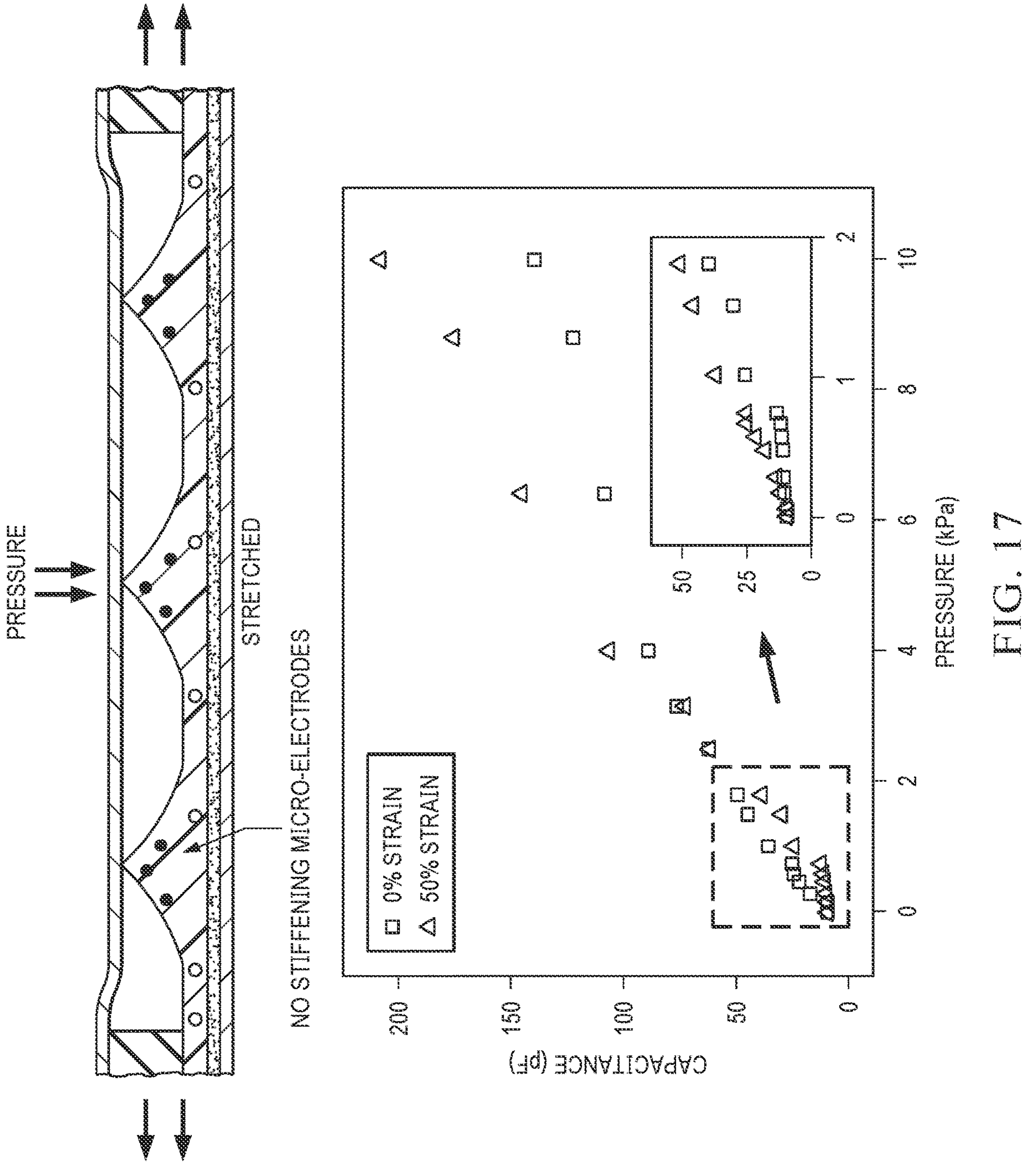

FIG. 17 shows pressure-sensing performance under stretching from a reference sensors that does not include stiffening electrodes.

Figure 18A:
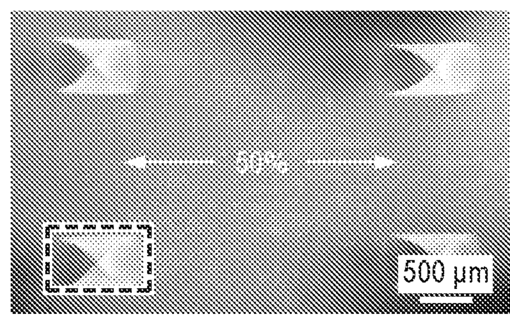
Figure 18B:
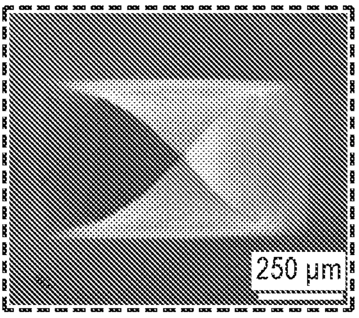
Figure 18C:
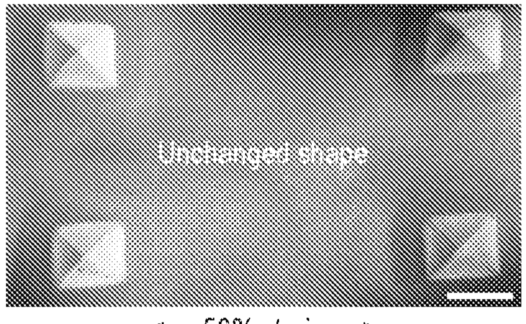

FIGS. 18A and 18B show scanning-electron microscopy (SEM) images of peaked structures (pyramids in this example) exposed to 50% in-plane strain that do not include stiffening electrodes, while FIG. 18C shows a SEM image of peaked structures (pyramids) exposed to 50% in-plane strain that are reinforced with the stiffening electrodes (FIG. 18C).

Figure 19:
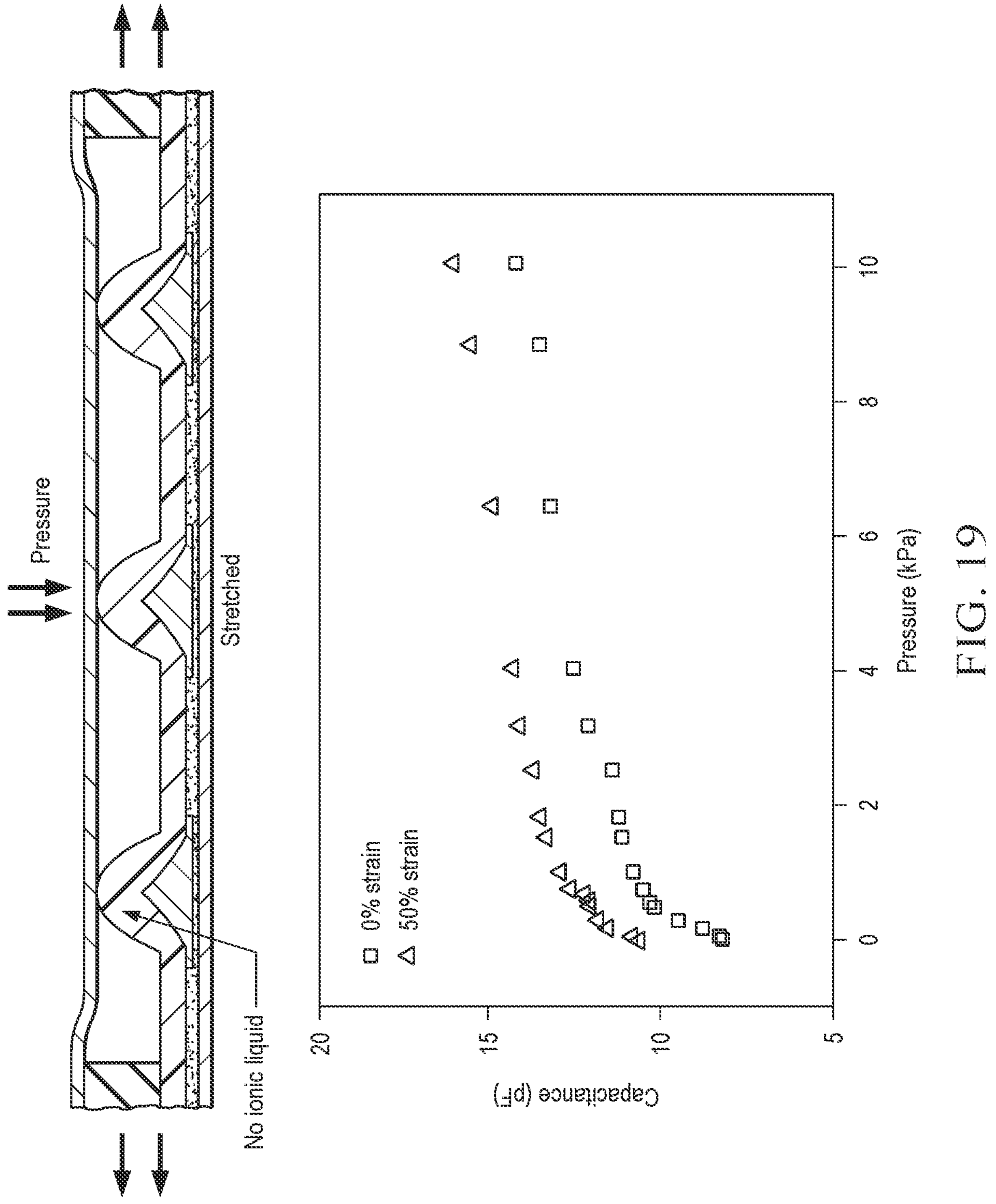

FIG. 19 shows pressure-sensing performance under stretching from a reference sensor having a continuous film that does not comprise an ionic liquid.

Figure 20:
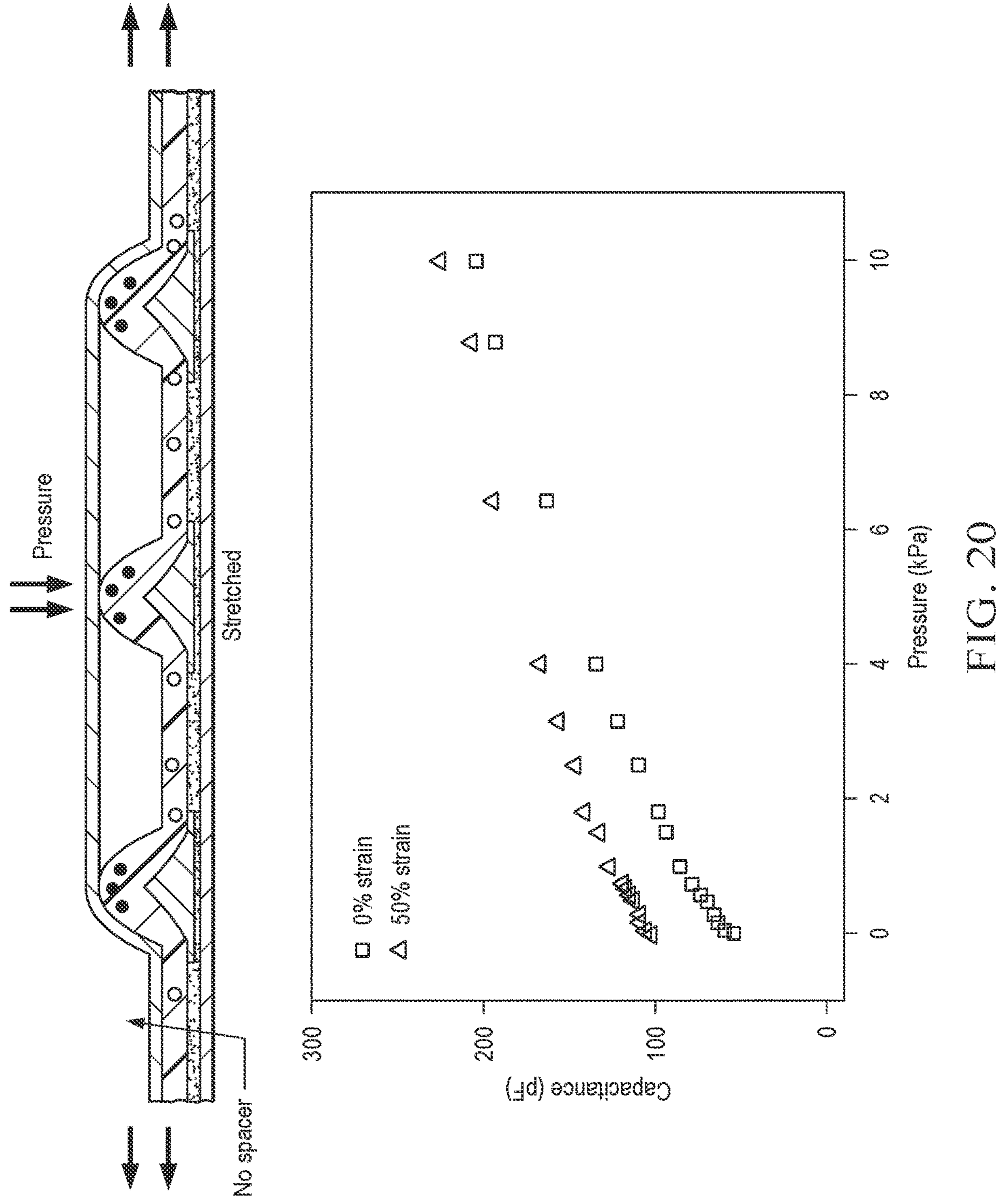

FIG. 20 shows pressure-sensing performance under stretching from a reference sensor that does not include soft spacers between the top electrode and the continuous film.

Figures 21, 22:
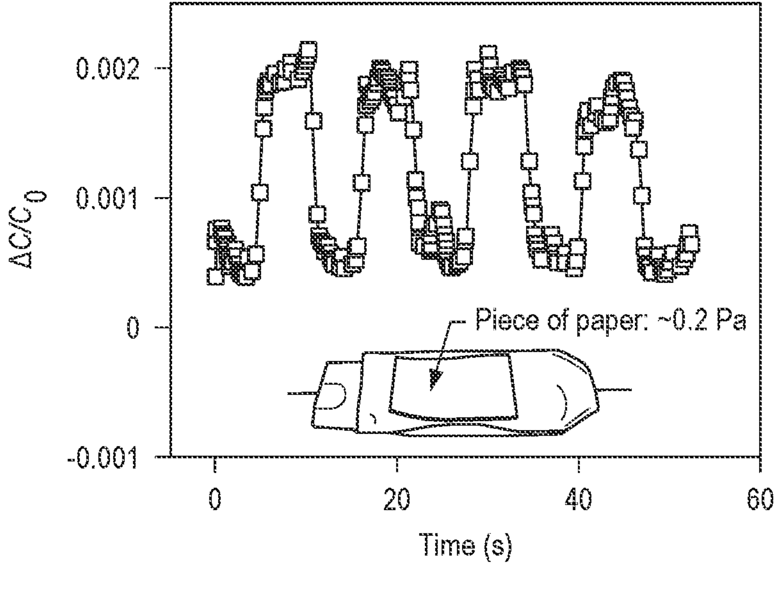

FIG. 21 shows capacitance response of an exemplary soft sensor under a pressure at the level of its limit of detection (about 0.2 Pa), where the pressure is created by a small piece of paper placed on the sensor (see inset).

FIG. 22 shows that the soft sensor is capable of recognizing small changes of pressure (e.g., by 30 Pa) on top of a large pressure (e.g., 1 kPa), when at both 0% and 50% strains.

Figure 23:
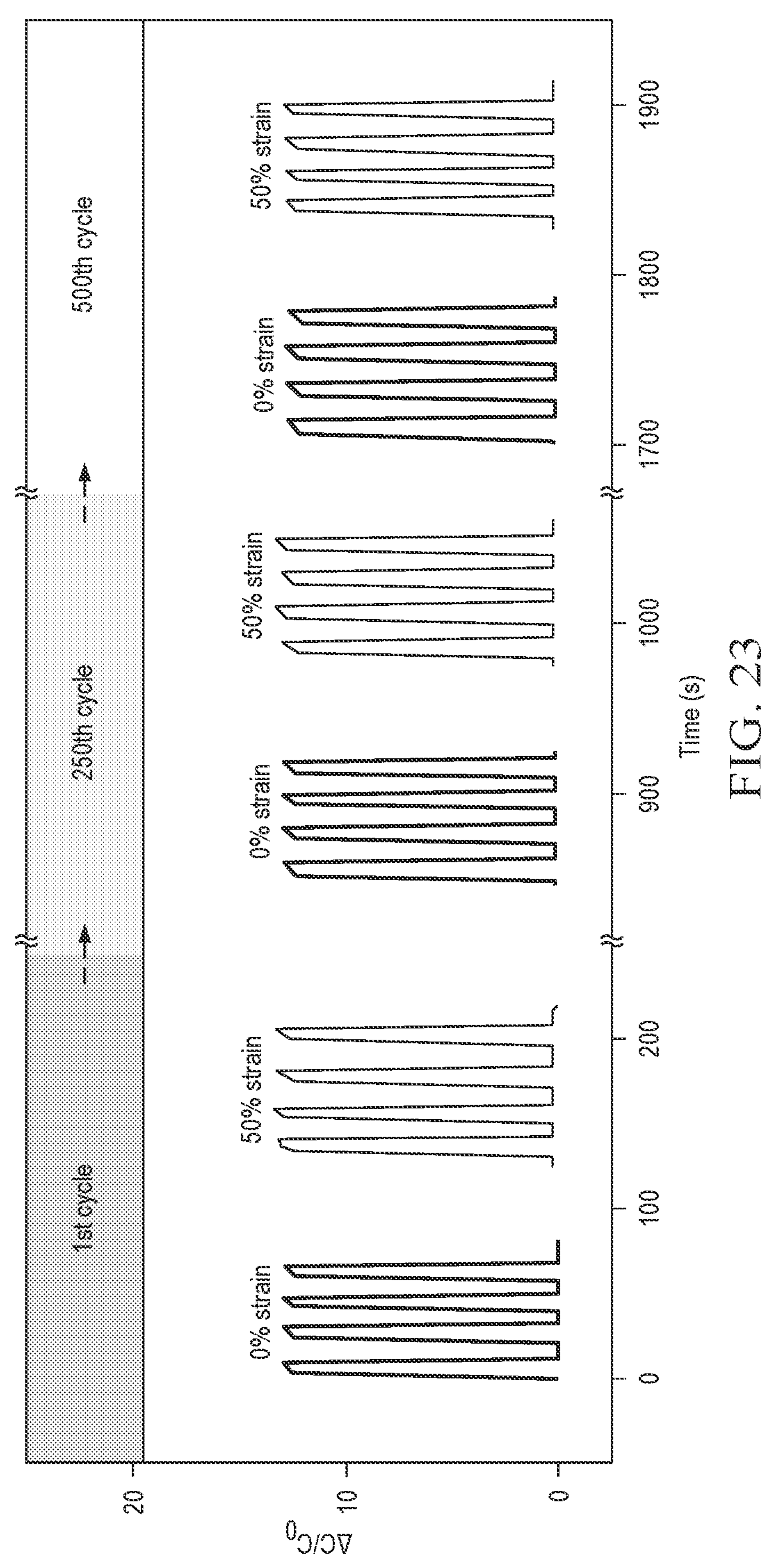

FIG. 23 shows fatigue test results of the sensor with 500 cycles of repeated stretching to 50% strain and pressure loading of 4 kPa.

Figure 24:
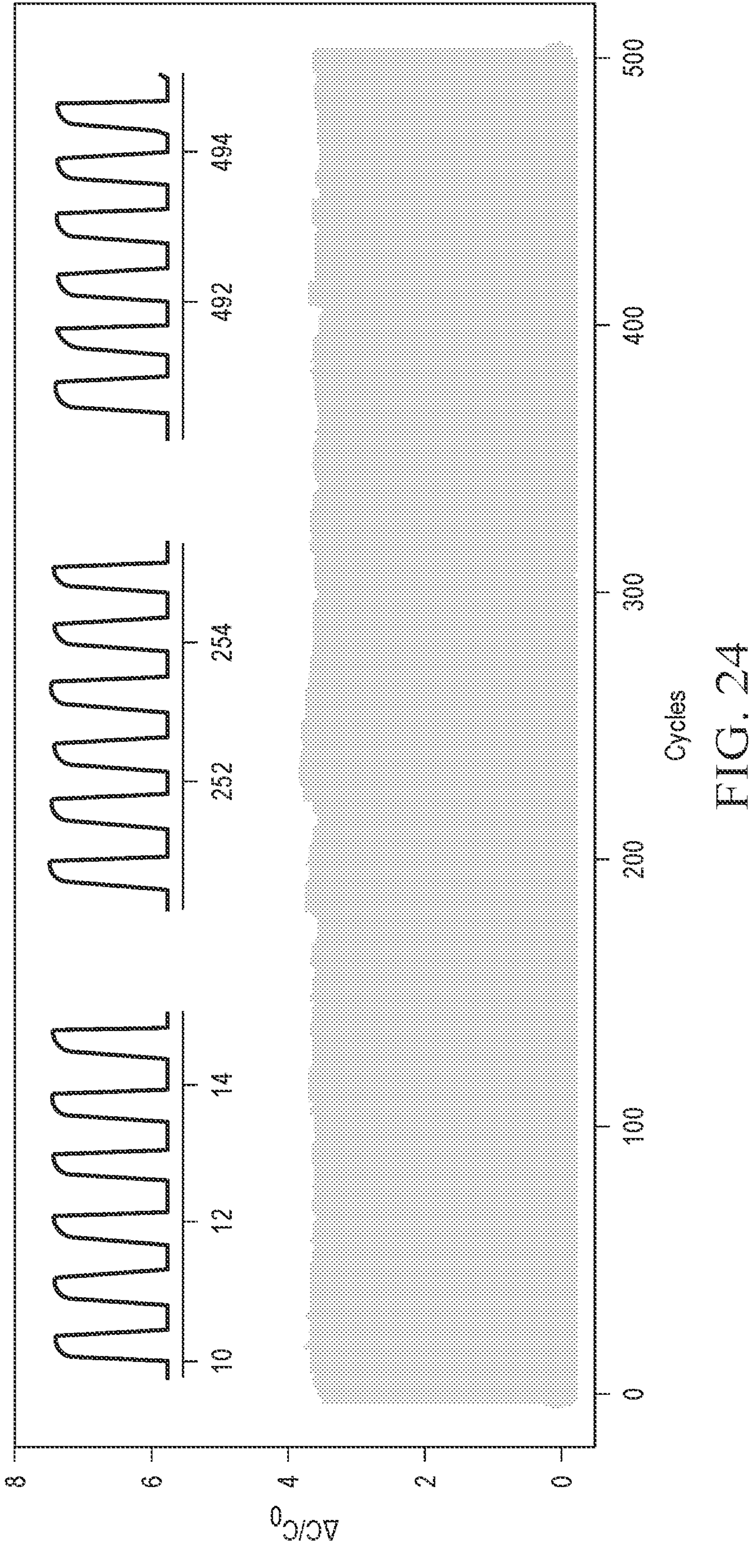

FIG. 24 shows fatigue testing results with 500 cycles of repeated pressure loading of 0.67 kPa under 0% strain.

Figure 25:
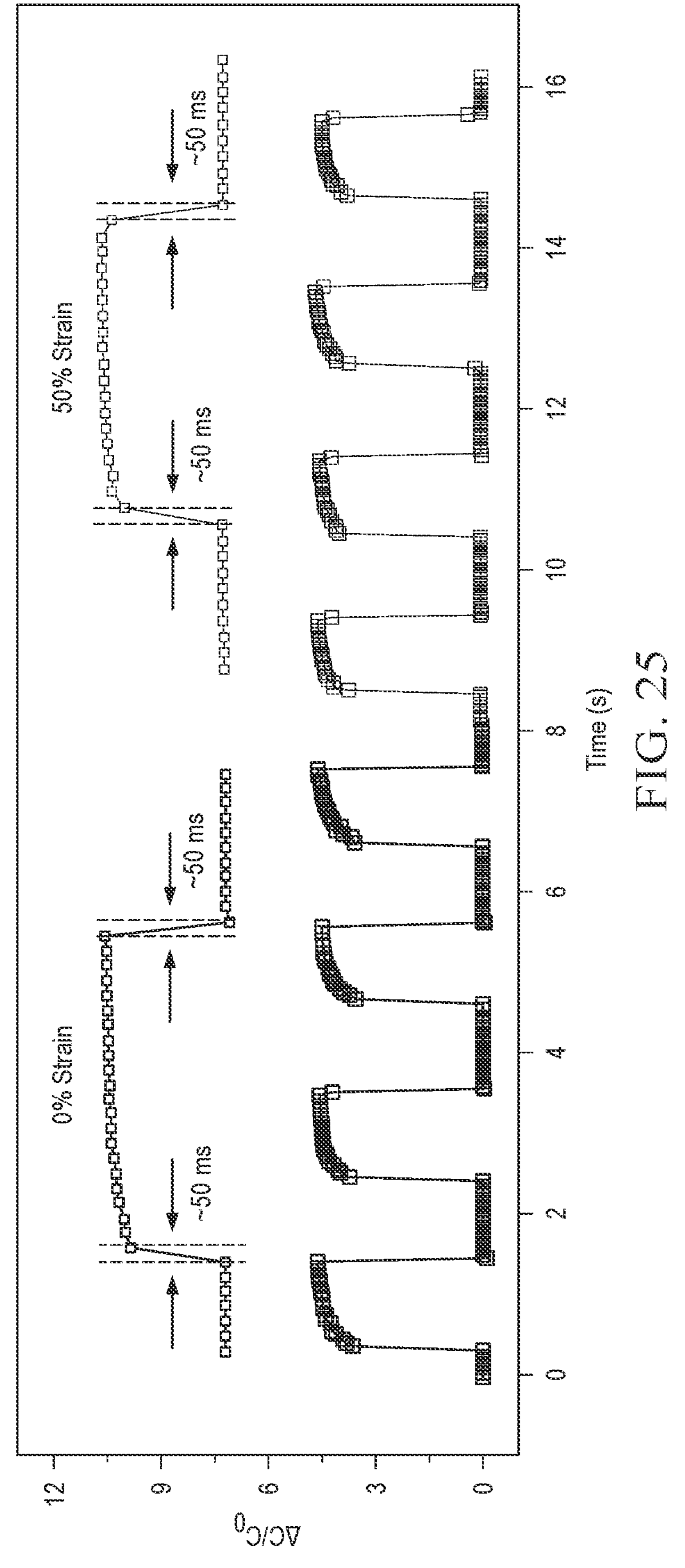

FIG. 25 shows response speed of the sensor at both 0% (left) and 50% strains (right).

FIGS. 26A-26L show steps in an exemplary process to fabricate the soft pressure sensor.

FIGS. 27A-27J show steps in an exemplary process to fabricate the top and bottom electrodes of the soft pressure sensor.

Figures 28A, 28B, 28C:
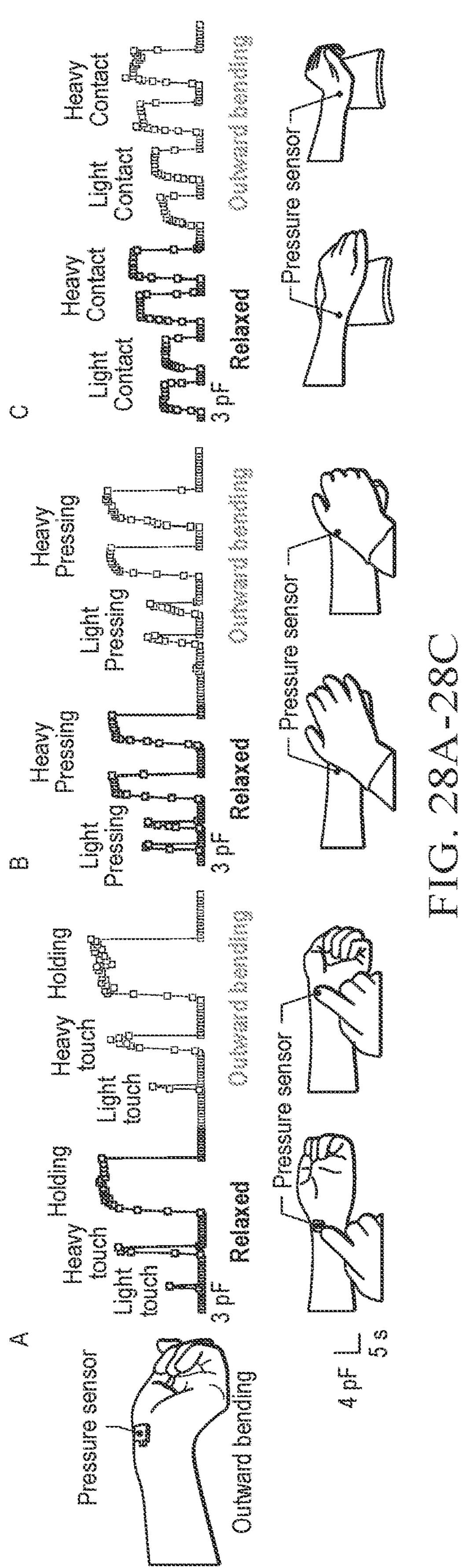

FIGS. 28A-28C show the sensor serving as a secondary electronic skin on a human (or prosthetic) wrist for providing quantitative sensation to various types of touches, including finger touch, hand palm touch, and touch with a soft object, when the wrist is in both the relaxed and outward-bending positions.

Figures 29A, 29B:
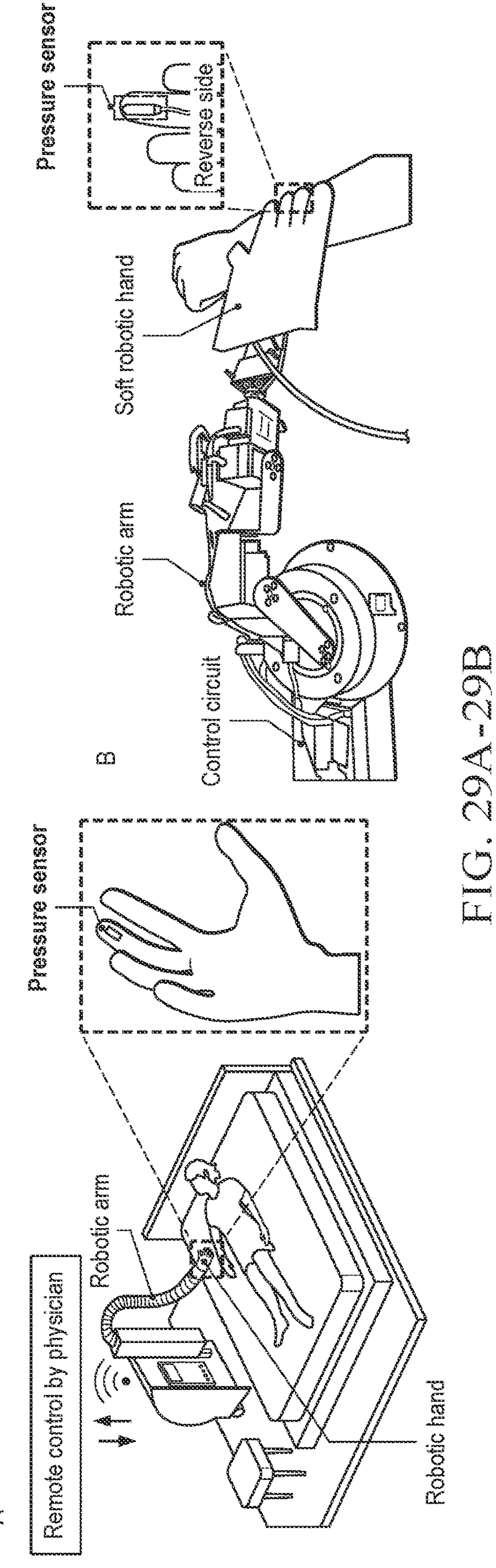

FIGS. 29A and 29B show a scenario of using the stretchable pressure sensor on a soft robotic hand to realize remote physical diagnosis and therapy on patients, including the experimental setup for demonstrating the stretchable pressure sensing enabling the soft robotic hand to apply a pre-set pressure to a human arm.

Figure 29C:
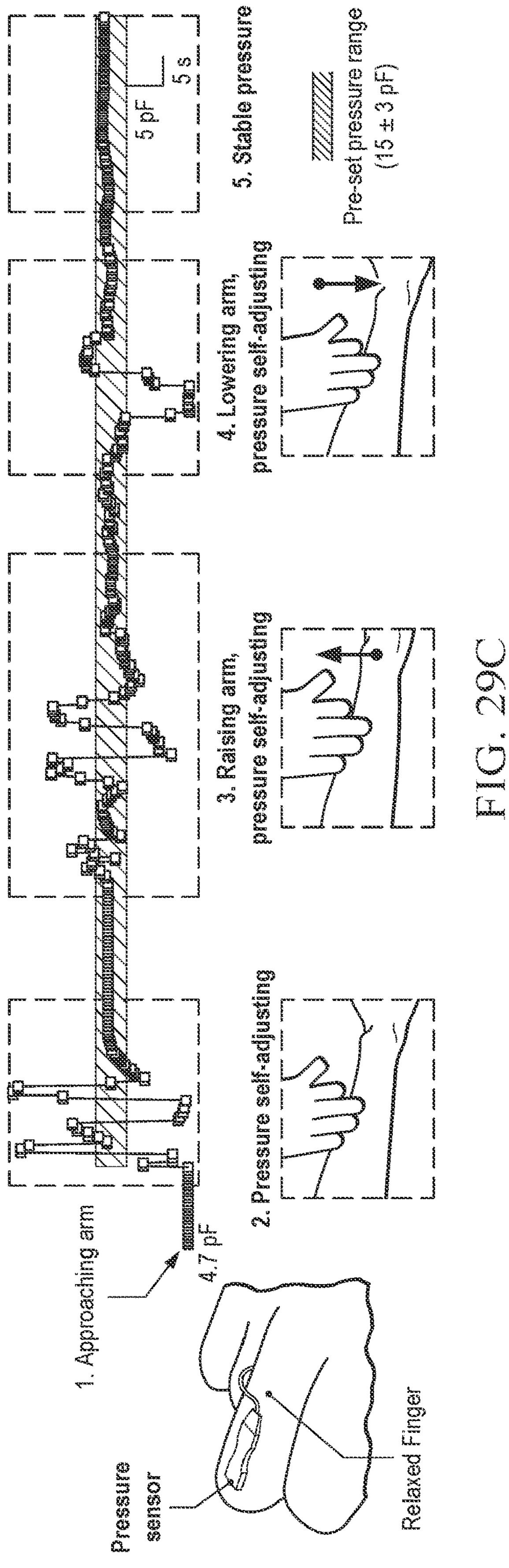

FIG. 29C shows a real-time capacitance reading from the pressure sensor integrated on a soft-robotic fingertip, which enables the closed-loop control of its attached robotic arm for applying and self-adjusting a force, with a pre-set pressure value, onto the top surface of a human arm.

Figure 29D:
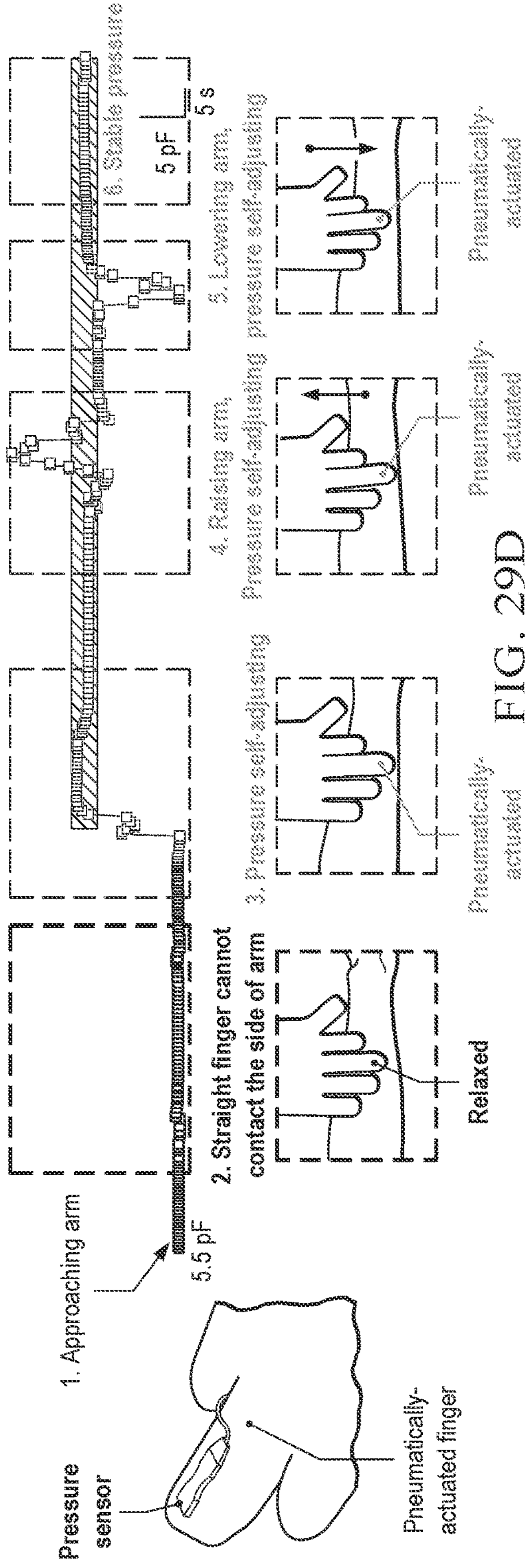

FIG. 29D shows a similar process as in FIG. 29C recorded for the robotic finger applying and self-adjusting a force to the side of the arm, during which the robotic finger bends through pneumatic actuation (thereby inducing stretching of the soft sensor).

FIGS. 30A-30D show cross-sectional schematics of an exemplary soft resistive pressure sensor in an unstretched state with no applied pressure, a stretched state with no applied pressure, an unstretched state with an applied (normal) pressure, and a stretched state with an applied (normal) pressure, respectively.

The drawings described herein are for illustration purposes only and are not intended to limit the scope of the present disclosure in any way.

DETAILED DESCRIPTION

Described in this disclosure is a highly-stretchable soft capacitive pressure sensor that may achieve strain-insensitive performance while providing a high pressure sensitivity of about 2 $kPa^{-1}$ or better, a high response speed, and repeatable and robust sensing performance. This performance may be enabled by the synergistic creations of an electrical double-layer (EDL) based capacitive sensing mechanism, a peaked (e.g., pyramidal, conical, or domed) microstructure with stiffness heterogeneity, and soft spacers. The stretchability and low modulus of the soft pressure sensor allows it to be attached to the human body or to robots with excellent conformability. The combination of the stretchable pressure sensor with a soft robotic hand has been demonstrated for quantitative and closed-loop pressure control (e.g., for remote medical palpation and therapy) and the pressure sensor has been shown to be useful as a secondary e-skin, as described below. A highly-stretchable soft resistive pressure sensor with a similar structure and capabilities has also been developed and is described later in this disclosure.

Figure 1:
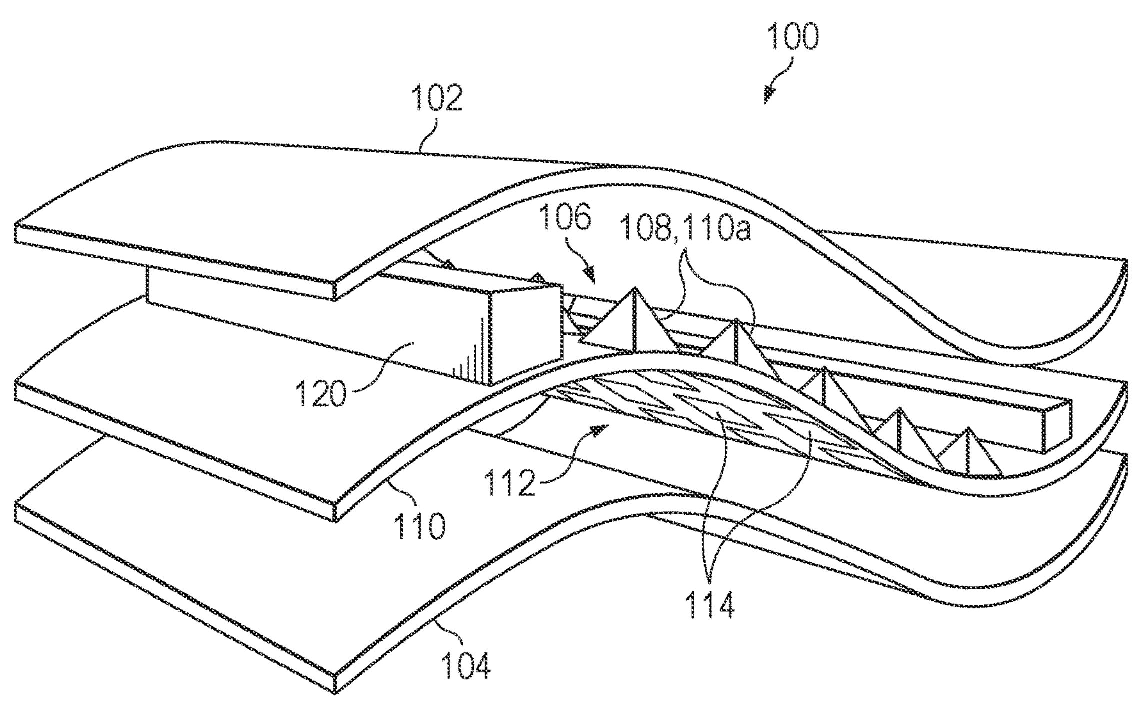
Figure 2:
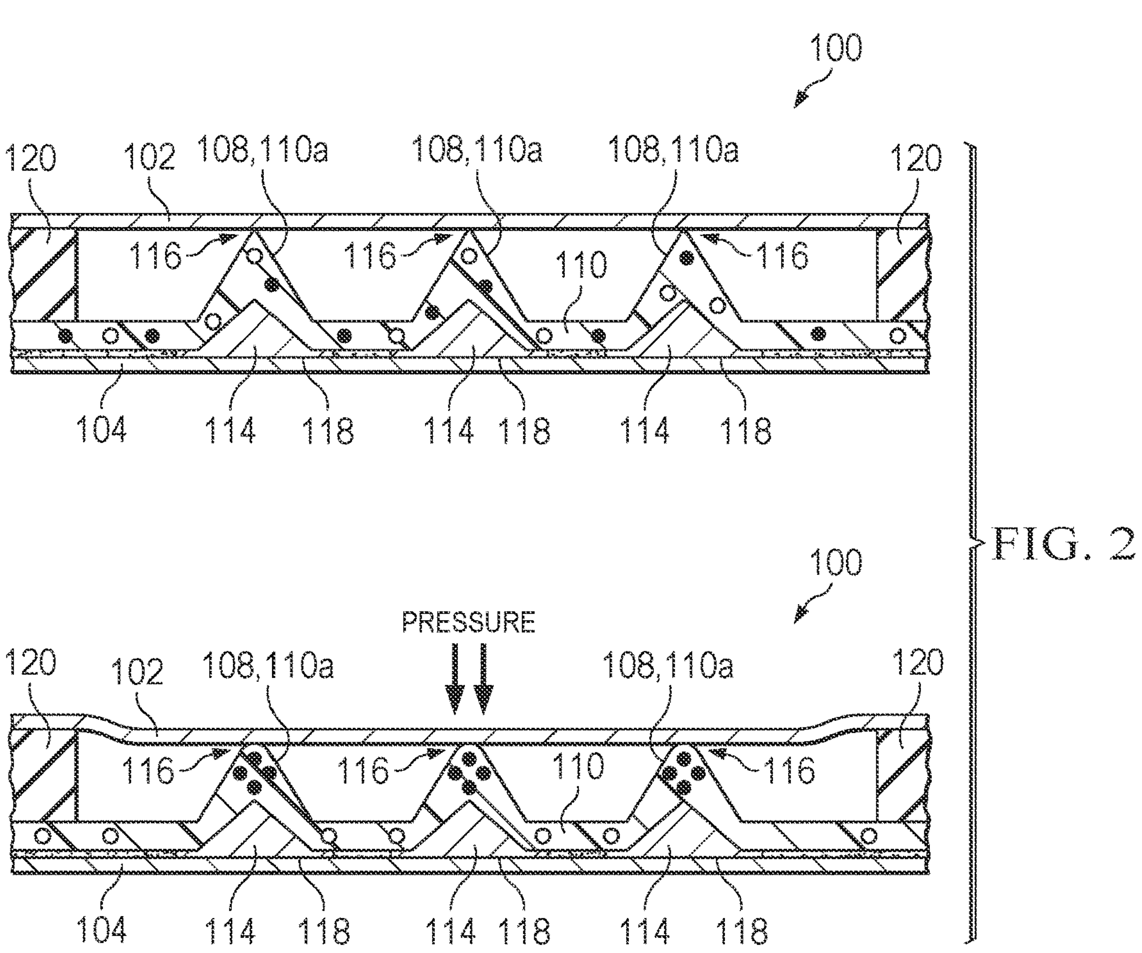
FIG. 2 is a cross-sectional schematic of an exemplary soft pressure sensor in an unstretched or relaxed state before (top) and after (bottom) exposure to an external pressure.

Referring to FIGS. 1 and 2, the soft capacitive pressure sensor 100 may comprise a stretchable top electrode 102, a stretchable bottom electrode 104, and an array 106 of peaked structures 108 between the stretchable top and bottom electrodes 102,104. The peaked structures 108 are defined by protruding regions 110*a* of a continuous film 110 that conformally overlie an array 112 of stiffening electrodes 114 on the stretchable bottom electrode 104. As shown in FIG. 2, an apex or tip 116 of each protruding region 110*a* is in contact with the stretchable top electrode 102, and a base 118 of each stiffening electrode 114 is in contact with the stretchable bottom electrode 104. The peaked structures 108 and, optionally, the stiffening electrodes 114 may have a pyramidal, conical, dome-shaped ("domed") or other three-dimensional shape having an apex that widens to a broader base, where the apex has a small radius of curvature (e.g., 0-30°) to ensure a small region of contact between the protruding regions 110*a* and the stretchable top electrode 102. Alternatively, the stiffening electrodes 114 may have a flat or non-peaked shape. The array 106 may comprise a one- or two-dimensional array that typically includes from 2 to 200 peaked structures 108. The peaked structures may have microscale dimensions with individual heights and widths typically in the range from 100-800 microns. One or more spacers 120 positioned outside the array 106 extend between and are bonded to the stretchable top electrode 102 and the continuous film 110 to help maintain the spacing of the top and bottom electrodes 102,104 under stretching deformation.

Figure 3:
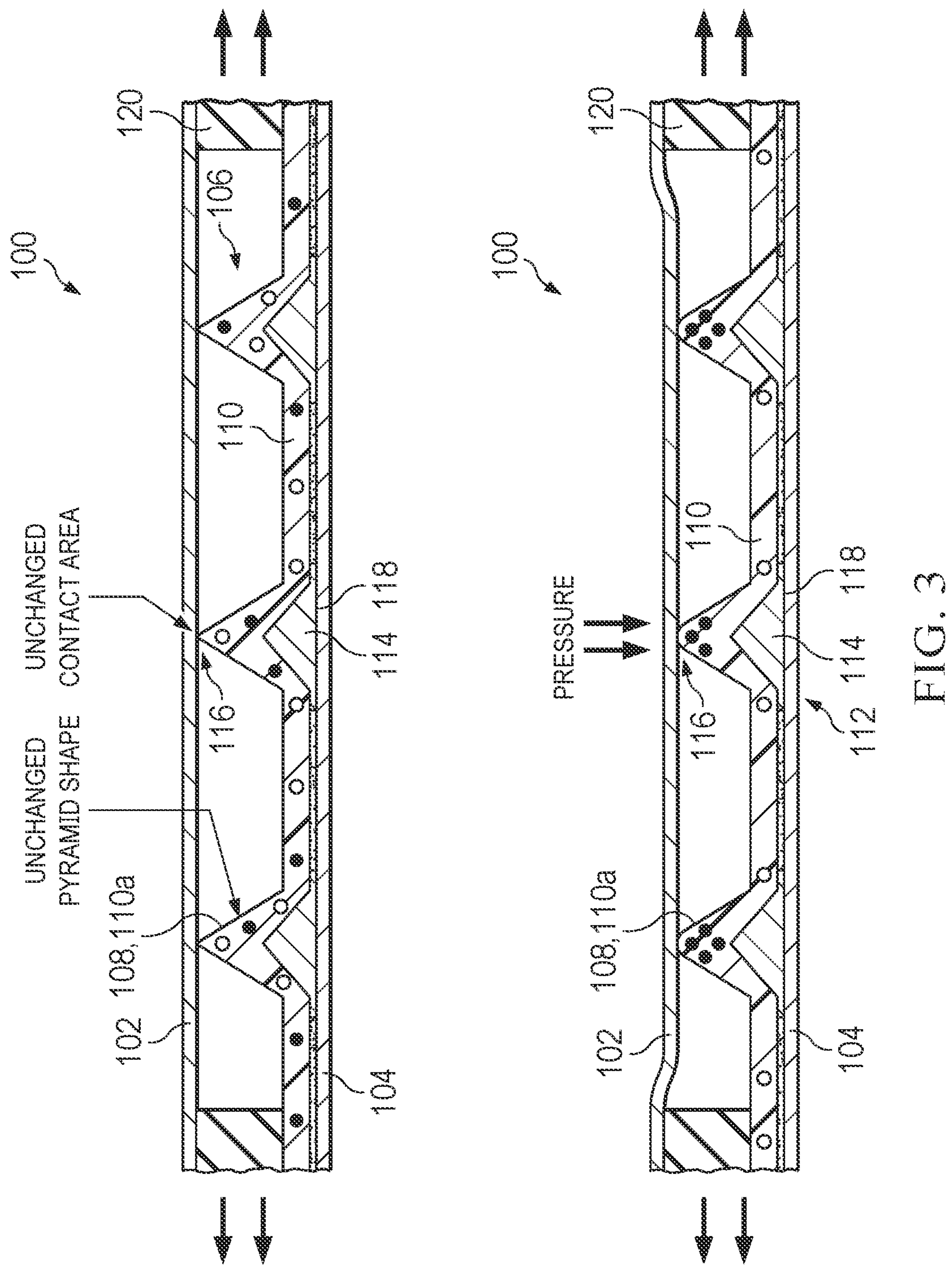
FIG. 3 is a cross-sectional schematic of the soft pressure sensor of FIG. 2 in a stretched state before (top) and after (bottom) exposure to an external pressure.

The soft pressure sensor 100 of FIG. 2 is shown undergoing in-plane stretching in FIG. 3 with and without an applied pressure (top and bottom schematics, respectively). Notably, the contact area between the tip 116 of each protruding region 110*a* and the stretchable top electrode 102, as well as the shape of each peaked structure 108, are substantially unchanged during deformation. Accordingly, a capacitance measured by the soft pressure sensor 100 is substantially invariant under in-plane stretching and/or bending. Consistent with data discussed below, a capacitance that is "substantially invariant" (or "substantially unchanged") under in-plane stretching and/or bending varies by about 2% or less on average while the soft pressure sensor 100 is undergoing in-plane stretching and/or bending.

Figure 4:
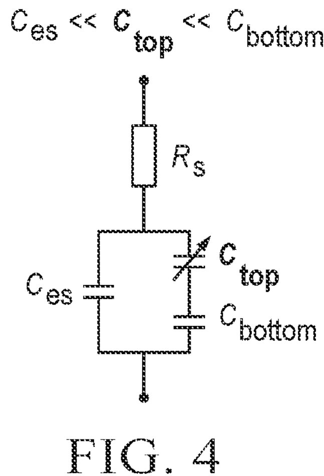
FIG. 4 shows an equivalent circuit for an exemplary soft pressure sensor.
Figures 5A, 5B:
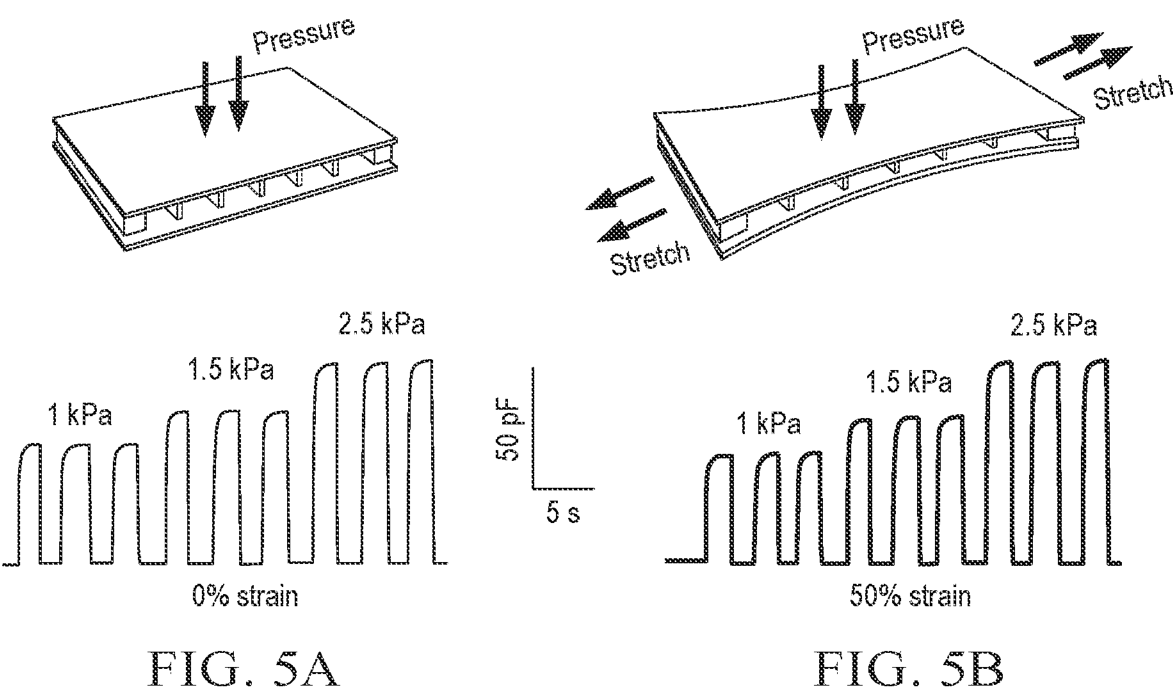
FIGS. 5A and 5B show schematic illustrations (top) of the soft pressure sensor of FIG. 1 operating under unstretched and stretched states, respectively, and the capacitance responses as the sensing signal to three repeated pressure values (bottom) when the sensor is unstretched (0% strain) and stretched (50% strain), respectively.

The continuous film 110 may comprise an ionically conductive elastomer. The use of an ionically conductive elastomer (which may also be referred to as an "ion gel" and/or an "ionic elastomer") for the continuous film 110 (and consequently for the protruding regions 110*a* and the tips 116) may ensure that the overall capacitance measured by the soft pressure sensor 100 is dominated by an electric double layer (EDL) capacitance formed at interfaces between the tips 116 and the stretchable top electrode 102. This is shown as $C_{top}$ in the equivalent circuit illustrated in FIG. 4, where $C_{es}$ is the electrostatic capacitance between the top and bottom electrodes 102,104, and $C_{top}$ and $C_{bottom}$ are the EDL capacitances of the top interface and the bottom interface between the ionic conductive elastomer at the tips 116 and the top electrode 102, respectively. As indicated above, this capacitance may remain substantially unchanged under in-plane stretching, enabled by the presence of the stiffening electrodes 114 within the peaked structures 108 and also the spacers 120 positioned outside the array 106, which help to maintain the spacing between the top and bottom electrodes 102,104 under stretching deformation. Consequently, under different strain states, as illustrated for example in FIGS. 5A and 5B, the soft pressure sensor 100 can maintain not only a highly stable capacitance value when there is no pressure, but also the same capacitance changing behavior in response to different pressures, as shown by the experimental data.

When a normal pressure is applied on the soft pressure sensor 100, the peaked structures 108 may be compressed vertically, thus increasing the contact area between the tips 116 and the top electrode 102, as can be seen by comparing the top and bottom schematics of FIG. 2. Therefore, a change in the capacitance value measured by the sensor 100, which is dominated by the EDL capacitance, may monotonically reflect the magnitude of the applied pressure. Compared to the commonly used electrostatic capacitance for pressure sensing, such EDL-type capacitance can provide much higher sensitivity. More uniquely, with this sensing mechanism, when the sensor 100 is under in-plane stretching, the capacitance value may remain unchanged (or substantially unchanged) because the design, which may include spacers 120 as shown, allows for a constant or nearly constant contact area between the peaked structures 108 and the top electrode 102 while under strain.

Contributing to this capability are the stiffening electrodes 114 that underlie the protruding regions 110*a* of the continuous film 110 and have a considerably higher stiffness (e.g., 0.3 GPa or higher) than the stretchable continuous film 110 (e.g., the ionic elastomer). Advantageously, the stiffening electrodes 114 may exhibit a stiffness or modulus of at least about 1 GPa, or at least about 3 GPa. The stiffening electrodes may include conductive and adhesive materials. In one example, the stiffening electrodes 114 may comprise an electrically conductive epoxy. Conductivity is beneficial so that the stiffening electrodes 114 act as an extension of the bottom electrode 104 and do not change the dominating role of the EDL at the top interface in the overall capacitance. With this design, strain applied to the soft pressure sensor 100 leaves the geometry of the peaked structures 108 virtually unaltered, such that the peaked structures 108 may maintain the same mechanical response to normal pressures independent of the strain state. In addition, one or more spacers 120 (two in this example) having the same height as the peaked structures 108 can help to minimize or eliminate possible strain-induced squeezing between the top and bottom substrates 102,104. The unaltered pressure sensing performance is confirmed by finite-element simulations, in which the relationship between the contact area and the pressure is identical at different strains, as shown in FIG. 6.

It has been demonstrated that the pressure sensor 100 may be stretched to at least 50% strain before the continuous film 110 starts to delaminate from the bottom electrode 104. As shown by the data of FIG. 7, the performance of the soft sensor 100 is systematically characterized under the stretching states of 0%, 25% and 50% strains, each with a pressure range of 0-10 kPa. The resulting signal is the capacitance of the sensor, measured at 1 kHz. Notably, the pressure sensing behaviors from four samples of separately fabricated sensors show good linearity over the entire pressure range when they are at 0% and 50% strains, with virtually identical performance, and a high sensitivity of 2.2 $kPa^{-1}$, as revealed by FIG. 8. Most importantly, when these pressure sensors 100 are stretched from 0% to 50% strain, almost no change in performance is observed. From a more quantitative analysis, the capacitance readings for different pressures applied with no strain and then with 50% strain vary by only about 2% on average; this can be regarded as a strain-insensitivity of 98%. Moreover, this strain-decoupled pressure sensing performance is well maintained during repeated stretching cycles to 50% strain, as demonstrated in FIG. 9. Through finite-element simulations, it is shown that the strain-insensitive pressure sensing can be obtained with varied peaked structure (e.g., pyramid) densities, that is, with varied spacings between adjacent peaked structures 108. Thus, the density or spacing of the peaked structures 108 may serve as a structural variable by which the sensitivity and the sensing range can be tuned to meet the requirements of different applications.

The structure of the soft pressure sensor 100 is now further described. As stated above, the continuous film 110 may comprise an ionically conductive elastomer or ion gel. Such a continuous film 110 may be prepared from, in one example, an ionic liquid, an elastomer, and an optional crosslinker, as described below. In another example, the continuous film 110 comprising the ion gel may be prepared from an electrolyte salt, a monomer, and optionally a crosslinker and/or a photoinitiator. In the first example, the elastomer may be a dielectric elastomer with, in some examples, a dielectric constant of at least about 7 or 8 to facilitate ion delocalization. The ionic liquid may comprise 1-ethyl-3-methylimidazolium bis(trifluoromethylsulfonyl) imide (EMIM:TFSI), the elastomer may comprise poly (vinylidene fluoride-co-hexafluoropropylene) (PVDF-HFP), which has a dielectric constant of about 9, and the optional crosslinker may comprise hexamethylenediamine (HMDA). When such an ionic elastomer is fabricated into capacitors, it is found that a higher amount of the ionic liquid blended into the elastomer provides a higher capacitance, which is a favorable condition for achieving a higher sensitivity, as shown by the data in FIG. 11 for ionic liquid concentrations of 0 wt. %, 15 wt. %, 30 wt. % and 60 wt. %. However, high concentrations of the ionic liquid may be accompanied by an increase in viscoelastic behavior, which may prevent the continuous film 110 from reverting to its original dimension. Consequently, ionic liquid concentrations are preferably in a range from 15-45 wt. %, or from 25-35 wt. %. Notably, the crosslinker (e.g., HMDA) may help to restore the desired elasticity for reversible deformation. A cyclic stretching test shows that an increased amount of HMDA may help to suppress viscoelastic behavior and increase Young's modulus of the ionic elastomer. With an amount of crosslinker at or above 1 wt. %, the continuous film 110 can fully return to its original length after stretching, as indicated by the data in FIG. 12. However, it is found that the crosslinking may cause the EDL capacitance to decrease; consequently, a preferred amount of the crosslinker is about 1 wt. % (e.g., 0.8-1.2 wt. %).

The stretchable top electrode 102 may be rendered electrically conductive and stretchable by incorporating an electrically conductive film and/or electrically conductive particles on and/or within an elastomeric layer. In one example, as illustrated in FIG. 13, the stretchable top electrode 102 comprises a first (electrically) conductive layer 130 on a first elastomeric layer 132, where the apex 116 of each protruding region 110*a* of the continuous film 110 is in contact with the first conductive layer 130. Similarly, the stretchable bottom electrode 104 may be rendered electrically conductive and stretchable by incorporating an electrically conductive film and/or electrically conductive particles on and/or within an elastomeric layer. In the example of FIG. 13, the stretchable bottom electrode 104 comprises a second (electrically) conductive layer 134 on a second elastomeric layer 136, where the base 118 of each stiffening electrode 114 is in contact with the second conductive layer 134, which may comprise an electrically conductive adhesive 138, as discussed below in regard to FIG. 16A.

The stretchable top and bottom electrodes 102,104 may be formed, in one example, by coating electrically conductive particles (e.g., comprising silver, copper, gold, aluminum, and/or carbon) in the form of a paste (e.g., a mixture paste with elastomers) onto an elastomeric layer (e.g., comprising a silicone elastomer such as Ecoflex). In a particular example, a stretchable silver nanoparticle paste may be applied by blade-coating or other patterning techniques onto an elastomeric layer to achieve a stretchable and conductive top or bottom electrode 102,104, which may also have a low Young's modulus (e.g., about 100 kPa or less). In the case of the top electrode 102, a low modulus may ensure that the applied pressure can be effectively transduced to the compression of the peaked structures 108, which may be important for the strain-insensitive performance. Owing to the good stretchability of the exemplary silver paste and its strong adhesion to the elastomer, the top or bottom electrode 102,104 may be highly stretchable and may exhibit a minimal increase or no increase in resistance during 500 cycles of repeated stretching to 50% strain, as shown by the data of FIG. 14.

When pressure is applied on the top electrode 102, not only do the peaked structures 108 undergo deformation, but also the top electrode 102—in particular the first elastomeric layer 132—has a "coverage effect" on the tips 116 of the peaked structures 108, as illustrated in FIG. 15A. This coverage effect may depend primarily on the thickness of the first elastomeric layer 132. Typically, the first and second elastomeric layers 132,136 have a thickness in a range from about 20 microns to about 500 microns, and more typically the thickness is in the range from about 50 microns about 300 microns. Referring to the data of FIG. 15B, a sensor 100 with a thicker first elastomeric layer 132 may have a higher sensitivity at 0% strain. When the sensor with a thicker top electrode (e.g., 110 μm or 210 μm) is stretched to 50%, the top electrode becomes significantly thinner and may result in a remarkably lower coverage effect. Therefore, the sensitivity of the stretched sensors 100 may decrease.

As an alternative to the above-described embodiment where the continuous film 110 comprises an ionically conductive elastomer, it is contemplated that the continuous film 110 may comprise an electronically conductive elastomer. Accordingly, in this embodiment, the stretchable top electrode 102 may be ionically conductive instead of electrically conductive, as described above. For example, the stretchable top electrode may comprise an electrically conductive layer on a first elastomeric layer, where the first elastomeric layer comprises the ionically conductive elastomer. The apex of each protruding region of the continuous film, which may comprise the electronically conductive elastomer, is in contact with the first elastomeric layer, which may comprise the ionically conductive elastomer. The electronically conductive elastomer of the continuous film may comprise, in one example, an elastomeric matrix with electrically conductive particles dispersed therein and/or thereon. As in the above-described embodiment, the stretchable bottom electrode may comprise a second conductive layer on a second elastomeric layer, where the base of each stiffening electrode is in contact with the second conductive layer.

Referring again to FIGS. 1 and 2, the one or more spacers 120, which are employed to minimize or eliminate possible strain-induced compression between the top and bottom substrates 102,104, may be positioned on opposing sides of the array 106. In some examples, the one or more spacers 120 may be positioned on all sides of the array 106. The spacers may be discrete structures (e.g., shaped as pillars), or elongated or continuous structures (e.g., shaped as rods, as shown in FIG. 1). When employed on opposing sides or on all sides of the array 106, the spacers 120 may comprise a plurality of the discrete or continuous structures that partly or completely surround the array 106. Alternatively, a single spacer 120 that extends around the perimeter so as to completely surround the array 106 may be suitable. The one or more spacers 120 may comprise an elastomer, such as a silicon elastomer, e.g., polydimethylsiloxane (PDMS).

Referring now to the schematic of FIG. 16A, the soft sensor 100 may include an electrically conductive adhesive 138 between the continuous film 110 and the stretchable bottom electrode 104. Without the conductive adhesive 138, wrinkling of the continuous film 110 may occur due to incomplete contact with the bottom electrode 104, as illustrated by the schematic of FIG. 16B, and/or the inhomogeneous Young's modulus of the continuous film 110. If not prevented, wrinkling may increase the contact area between the top electrode 102 and the continuous film 110. As a consequence, the capacitance response at 50% strain may be higher than that at 0% strain, and this effect may be especially pronounced at pressures larger than 4 kPa. The presence of the conductive adhesive 138 may minimize or eliminate wrinkling of the continuous film 110, thereby improving the reliability of the capacitance response under strain. The adhesive 138 may comprise an electrically conductive paste applied to the bottom electrode 104 prior to assembly with the top electrode 102, the array 106 of peaked structures 108, and the one or more spacers 120, as described below.

To experimentally validate the roles of key design features—such as the stiffening electrodes 114, the EDL capacitance from tips 116 of the protruding regions 110*a* comprising the ionic elastomer and the soft spacers 120—several types of reference sensors, each without one of these features, were fabricated and characterized. Firstly, when the stiffening electrodes are not included, the stretching indeed non-negligibly alters the pressure sensing performance over the entire pressure sensing range. The capacitance readings taken under the same pressure with no stretching and at 50% strain can change by as much as 50%, as shown by the data of FIG. 17. This can be attributed to flattening of the peaked structures under in-plane stretching, which causes of the contact area with the top electrode to increase. The flattening is shown in FIGS. 18A and 18B for peaked structures (pyramids in this example) exposed to 50% in-plane strain that do not include the stiffening electrodes, in comparison with peaked structures (pyramids) exposed to 50% in-plane strain that are reinforced with the stiffening electrodes (FIG. 18C).

Secondly, a sensor is fabricated with peaked structures including a continuous film made from a non-ionic elastomer (in this example, PVDF-HFP), thereby turning the sensor into an electrostatic capacitor. Besides the expected decrease of the capacitance values and sensitivity, the pressure sensing performance also shifts under stretching, as shown by the data of FIG. 19. Although the stiffened pyramid structures are not subjected to stretching, there is still a slight decrease in the distance between the top and bottom electrodes in the areas between the pyramids, as well as an increase in the overlapped area between the top and bottom electrode, which overall serve to determine the electrostatic capacitance.

Lastly, when the spacers are not included in the design of the soft sensor, strain-insensitive pressure-sensing performance cannot be achieved, due to the non-ideal contact between the pyramids and the top electrode at the two ends of the sensors, as shown by the data of FIG. 20.

The main performance characteristics of the soft sensor 100, including its pressure detection limit, stability, and response time, also have been characterized. Through testing the sensor performance under ultralow pressure, a detection limit as small as about 0.2 Pa (e.g., the pressure created by a small piece of paper placed on the sensor) is obtained, as shown by the data of FIG. 21. In addition, referring to the data of FIG. 22, even when the sensor is operating under a relatively high pressure (e.g., 1 kPa), it still has very good recognition to small changes of pressure (e.g., by 30 Pa) on the top, under both strain-free and stretched conditions, which reflect the accuracy and steadiness of the sensing performance. To test the stability of the performance of the soft sensor, repeated stretching to 50% strain for 500 cycles is applied, as shown by the data of FIG. 23, and repeated pressure loading with 0.67 kPa for 500 cycles under 0% and 50% strain, as shown by the data of FIG. 24, where the insets display signals from cycles 10-15, 250-256, and 490-496. In both cases, no changes in either the pressure-sensing performance or the strain-insensitive characteristics were observed. Moreover, the dynamic sensing performance has a short response time of ~50 ms to both the loading and unloading of pressure, as shown by the data of FIG. 25, which is not impacted by stretching either. When compared with previously reported stretchable pressure sensors, the soft sensor described in this disclosure is the only one to attain all the three key performance characteristics simultaneously: low detection limit (i.e., high sensitivity) for pressure, high stretchability, and strain-insensitive performance.

Fabrication of the soft pressure sensor 100 is described below in reference to FIGS. 26A-26L and 27A-27J.

Figures 26A, 26B, 26C, 26D, 26E, 26F, 26G, 26H, 26I, 26J, 26K, 26L:
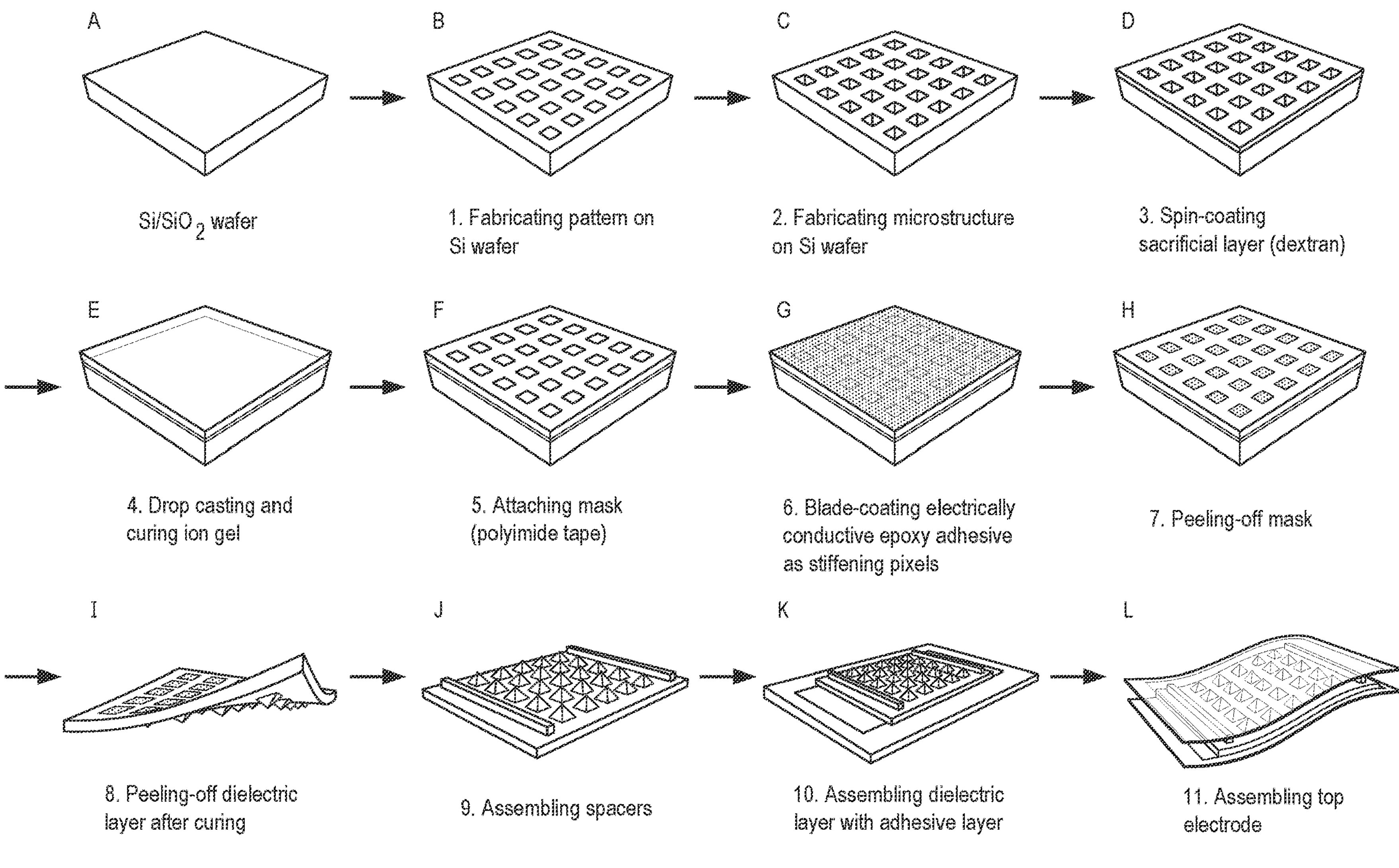

The protruding regions of the continuous film and the stiffening electrodes may be formed using a mold, such as a silicon mold as described here. To create the mold, a layer of photoresist (e.g., AZ 703) may be spin-coated on a $Si/SiO_2$ wafer, as shown in FIG. 26A. After baking and exposure, the $Si/SiO_2$ wafer may be patterned (e.g., by reactive-ion etching) to produce an array of opened windows, each of which may be several hundred microns in width or diameter (e.g., covering an area of 500×500 $\mu m^2$) with exposed Si, as shown in FIG. 26B. Next, an array of inverted peaked structures ("inverted array") with a height (depth) of several hundred microns (e.g., 200-500 microns, or more particularly 350 μm) may be formed by a method such as wet etching, as illustrated in FIG. 26C. For example, a TMAH solution (5 wt. % in $H_2O$) may be used for etching at 80° C. The surface of the mold may be modified (e.g., by $O_2$ plasma (400 W, 200 mTorr)) to enhance its hydrophilicity, and a sacrificial layer may be applied (e.g., by spin coating and then annealing), as illustrated in FIG. 26D. In one example, the sacrificial layer may comprise a polymer such as Dextran (e.g., 5 wt. % in water). The sacrificial layer may be spin coated onto the mold at 3000 r.p.m. for 30 s, followed by annealing at 80° C. for 10 minutes.

An elastomer/ionic gel is prepared to use as a precursor for forming the continuous film. An elastomer, such as PVDF-HFP, may be dissolved in acetone or another organic solvent. The elastomer to solvent weight ratio may be about 1:6, or more generally speaking in a range from about 1:5 to about 1:15. An ionic liquid, such as EMIM:TFSI, may be added into the mixture at a suitable weight percentage, such as from 15% to 60%, as further described above. The solution may be stirred at room temperature for a time duration of typically 2 h to 6 h. A crosslinker such as HMDA may be added into the elastomer/ionic liquid solution, first by dissolving the crosslinker in an organic solvent such as acetone at a suitable concentration (e.g., 20-200 mg/mL, or more particularly, 80 mg/mL), and then adding the mixture to the elastomer/ionic liquid solution and stirring, e.g., at 300 r.p.m for 10 min, thereby forming the elastomer/ionic gel.

To form the continuous film, the elastomer/ionic gel may be coated onto the mold, followed by curing, as shown in FIG. 26E. Conformal coating of the elastomer/ionic gel over the inverted peaked structure array leads to formation of the protruding regions of the continuous film. In one example, the elastomer/ionic gel may be drop-cast onto the mold and then cured at room temperature for several hours (e.g., 4 hours), to form the conformally coated continuous film, which may have a thickness in a range from about 60 μm to about 260 μm (e.g., 160 μm).

Subsequently, to form the array of stiffening electrodes, a mask may be placed on the continuous film such that its pattern aligns with the inverted array, as illustrated in FIG. 26F, and an electrically conductive polymer precursor may be applied over the mask and deposited into the inverted array, as shown in FIG. 26G. The application over the mask may comprise blade-coating over the continuous film and into the inverted array. In one example, a polyimide mask may be employed, and the electrically conductive polymer precursor may comprise an uncured electrically conductive epoxy adhesive. The mask may then be removed, followed by curing of the electrically conductive polymer precursor, as shown in FIG. 26H. Upon removal of the mask and curing, a stiffening electrode remains at what becomes the base of each peaked structure. Curing of the electrically conductive polymer precursor may be carried out using heat, light or another curing agent; in one example, curing takes place at 80° C. for 10 min. After curing, the sacrificial layer may be dissolved, and the continuous film may be peeled off the mold. Thus, the array of peaked structures is formed, as can be seen in FIG. 26I. A polymer film having a thickness comparable to or identical to that of the peaked structures may be cut into the desired shape and dimensions to serve as the soft spacer(s), and then bonded to the continuous layer, outside the array of peaked structures. In one example, a PDMS film with a thickness of 350 μm is employed and cut into two elongated pieces (14×4×0.35 $mm^3$) to serve as the soft spacers, which are bonded to the two short edges of the continuous film, 2 mm away from the array of peaked structures. This configuration is illustrated in FIG. 26J.

Figures 27A, 27B, 27C, 27D, 27E, 27F, 27G, 27H, 27I, 27J:
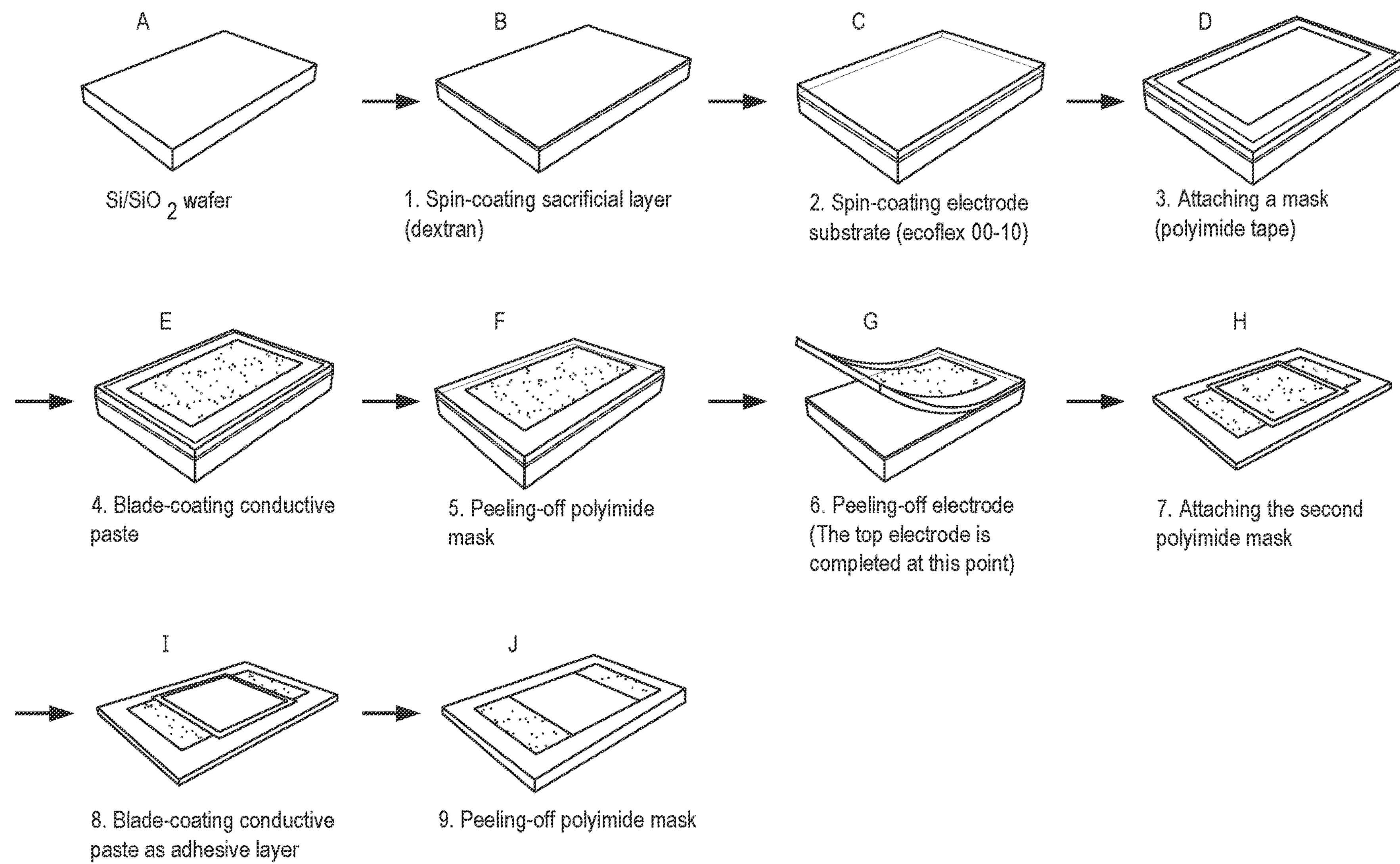

Referring now to FIG. 27A, to construct the bottom and top electrodes, $Si/SiO_2$ wafers or other suitable substrates may be coated with a polymeric sacrificial layer, such as a Dextran layer, as shown in FIG. 27B. An elastomeric coating, which in one example may be formed from Ecoflex 00-10 (part A:part B=1:1), may then be applied over the sacrificial layer, as illustrated in FIG. 27C. The sacrificial layer and the elastomeric coating may be applied by spin-coating or another deposition method known in the art. In one example, spin-coating may be carried out at 1500 r.p.m. for 30 s and/or at 3500 r.p.m. for 30 s. Next, a patterned mask (e.g., a polyimide mask) may be overlaid on and/or affixed to the elastomer-coated wafer, as shown in FIG. 27D, and an electrically conductive paste, such as an Ag nanoparticle paste layer, may be applied to a suitable thickness, such as about 20-60 μm, followed by curing, as illustrated in FIG. 27E. The application of the conductive paste may be carried out by blade-coating, in one example, and curing may comprising heating at a temperature in a range from about 120-170° C. (e.g., 150° C.) for a time duration of 10-50 min (e.g., 30 min), which yields an electrically conductive particle layer on the elastomer. The resulting stretchable electrode, shown in FIG. 27F after removal of the mask, may be peeled-off from the Si wafer or other substrate by dissolving the sacrificial layer, as illustrated in FIG. 27G. At this point, the stretchable top electrode is complete. To complete the stretchable bottom electrode, an additional mask, as shown in FIG. 27H, and an adhesive layer (e.g., an electrically conductive paste layer), as shown in FIG. 27I, may be applied to the electrically conductive particle layer on the elastomer by blade-coating or another method. Upon removal of the additional mask, as shown in FIG. 27J, the bottom electrode is ready for assembly to form the soft pressure sensor.

Referring now to FIG. 26K, the continuous film with peaked structures and spacers may be placed on top of the adhesive layer to form a lower part of the sensor, which then undergoes heating to bond the continuous film to the stretchable bottom electrode. The heating of the lower part of the sensor may include, in one example, pre-curing at 80° C. for 1 hour and then post-curing at 150° C. for 5 min, or another known curing protocol. Finally, the stretchable top electrode may be applied and bonded to the soft spacers to complete the soft pressure sensor, as illustrated in FIG. 26L.

The stretchability and strain-insensitive performance of the soft sensor allows for quantitative measurements of pressure at soft and deformable surfaces, such as human tissue/skin or soft robots. Described below are examples of leveraging the soft pressure sensor to enable precise measurement and control of pressure: (1) to digitally record touch information on human or prosthetic limbs, which may deform as they move; and (2) to quantitatively sensorize a pneumatically-actuated soft hand of a medical soft robot, allowing it to precisely calibrate a force-feedback controller to regulate the pressure applied onto patients' bodies.

The first representative application demonstrates the stretchable pressure sensor as a secondary e-skin, either on a human skin to digitally record touch information for the neurological understanding of mechanical sensation process, or on prosthetic limbs to accurately restore the touch sensation without being influenced by the limb's movements. To demonstrate this, a sensor with a dimension of 5×10 mm$^2$ is attached to the skin to measure various types of touch, even as the user's wrist bends. The high sensitivity of the sensor enables quantitative recognition of different types of touches, including finger touch (FIG. 28A), palm pressing (FIG. 28B) and contact with another soft object (FIG. 28C), with varied lightness and durations. Importantly, there is minimal change of capacitance signals resulting from the wrist bending under the same type of touch, which is afforded by the strain-insensitive performance of the soft pressure sensor.

The second representative application is on soft robots for patient/elderly care, physical diagnosis and therapy, which hinge on the precise control of the force applied in interactions between a robot and a patient's body. Through accurately measuring the pressure, in real-time, between the end-effector of a robotic soft hand and a human body during palpation or therapy, and sending the information to a remote system operated by a doctor, the doctor can then perform remote diagnosis and/or therapy through controlling the robotic hand to exert well-controlled pressures onto a patient's body, as illustrated in FIGS. 29A and 29B. To demonstrate this, a stretchable pressure sensor is attached to the fingertip of a pneumatically-actuated soft robotic hand that is connected to a motorized robotic arm for executing its movement. In this way, the soft robotic hand can be moved by the robotic arm to make contact and apply pressure to another object such as a human body in the scenario of physical therapy. To realize the programmed control of the pressure applied by the soft robotic hand, which is a core function needed in physical therapy, the stretchable pressure sensor can serve to provide real-time pressure values, which are fed to the closed-loop controller of the robotic arm, for achieving the desired pressure value. As shown in FIG. 29C, the soft robotic hand is first moved downward by the robotic arm to touch a human arm, and then it starts to quickly self-adjust its position to reach a pre-set pressure (e.g., 1.0±0.3 kPa, or 15±3 pF as the readout signal from the sensor). With the continuous monitoring of the pressure, this self-adjustment process restarts automatically whenever there is a movement of the patient's arm. In the case that the robotic finger needs to bend (e.g., through air inflation) to make contact to the side of the patient's arm, the strain-insensitive performance of the pressure sensor under stretching can ensure the unaltered function of pressure control and self-adjustment, as shown in FIG. 29D. Soft-robotic approaches are increasingly important as they enable remote diagnosis and therapy when doctors and patients are not physically collocated. In this case, the inventive stretchable and strain-insensitive pressure sensor provides a key, and much needed, function for this type of applications.

In view of these demonstrations, a method of measuring or monitoring pressure with the soft pressure sensor is described. The method includes attaching the soft pressure sensor as described according to any example or embodiment in this disclosure to a part or appendage of a human body or soft robot, contacting an object with the soft pressure sensor, and measuring a capacitance of the soft pressure sensor, thereby obtaining touch information during the contacting. The method may further include transmitting the capacitance measured by the soft pressure sensor to a closed loop controller and adjusting a position of the part or appendage with respect to the object to achieve a predetermined capacitance, and thus a preset pressure. Motion of the part or appendage may be automated. As the soft pressure sensor is stretched or bent to accommodate motion of the part or appendage, the capacitance measured by the soft pressure sensor is substantially unchanged. The capacitance may be an electric double layer (EDL) capacitance, as described above. The object may be an inanimate object, an animal or a human being.

By creating a design strategy that may synergistically combine EDL capacitance, the local stiffening obtained from stiffening electrodes, and the structural support of soft spacers, a stretchable pressure sensor is obtained that may provide all desired performance characteristics for quantitative pressure sensing—even when attached to a soft and/or deformable surface, such as human skin or soft robots. The soft sensor may exhibit high sensitivity to pressure, high stretchability, unaltered pressure sensing performance under stretching, good linearity over a wide pressure range, fast response speed, high repeatability and robust performance. Consequently, the strain-insensitive stretchable pressure sensor may be used to quantitatively sensorize and/or digitize the sensation on human, prosthetic and robotic skins.

Also described in this disclosure is a soft, stretchable resistive pressure sensor that can realize strain-unperturbed pressure sensing based on a similar design as the above-described capacitive sensor 100. FIGS. 30A-30D show cross-sectional schematics of an exemplary resistive pressure sensor 200 in an unstretched state with no applied pressure, a stretched state with no applied pressure, an unstretched state with an applied (normal) pressure, and a stretched state with an applied (normal) pressure, respectively.

Figures 30A, 30B:
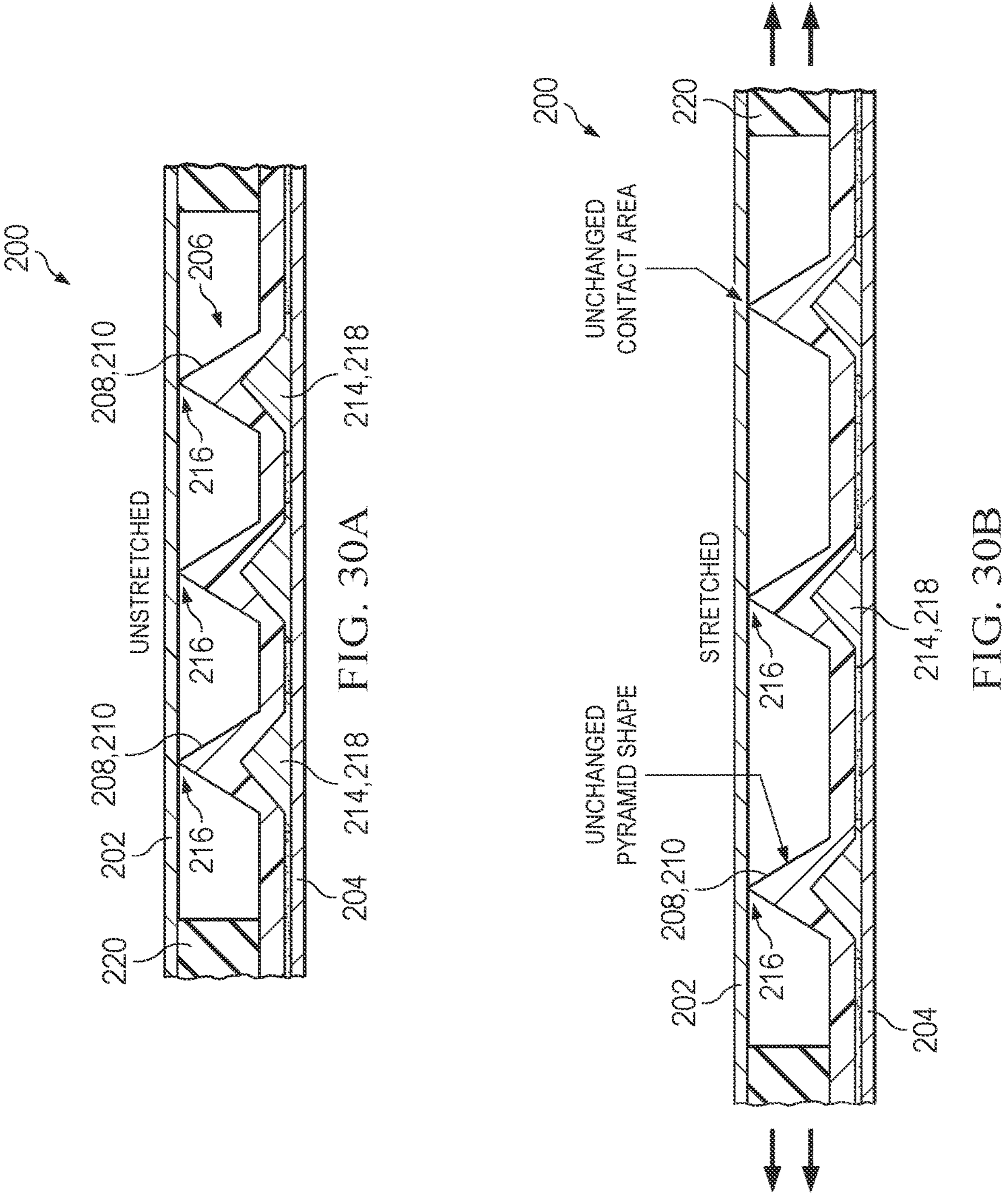
Figures 30C, 30D:
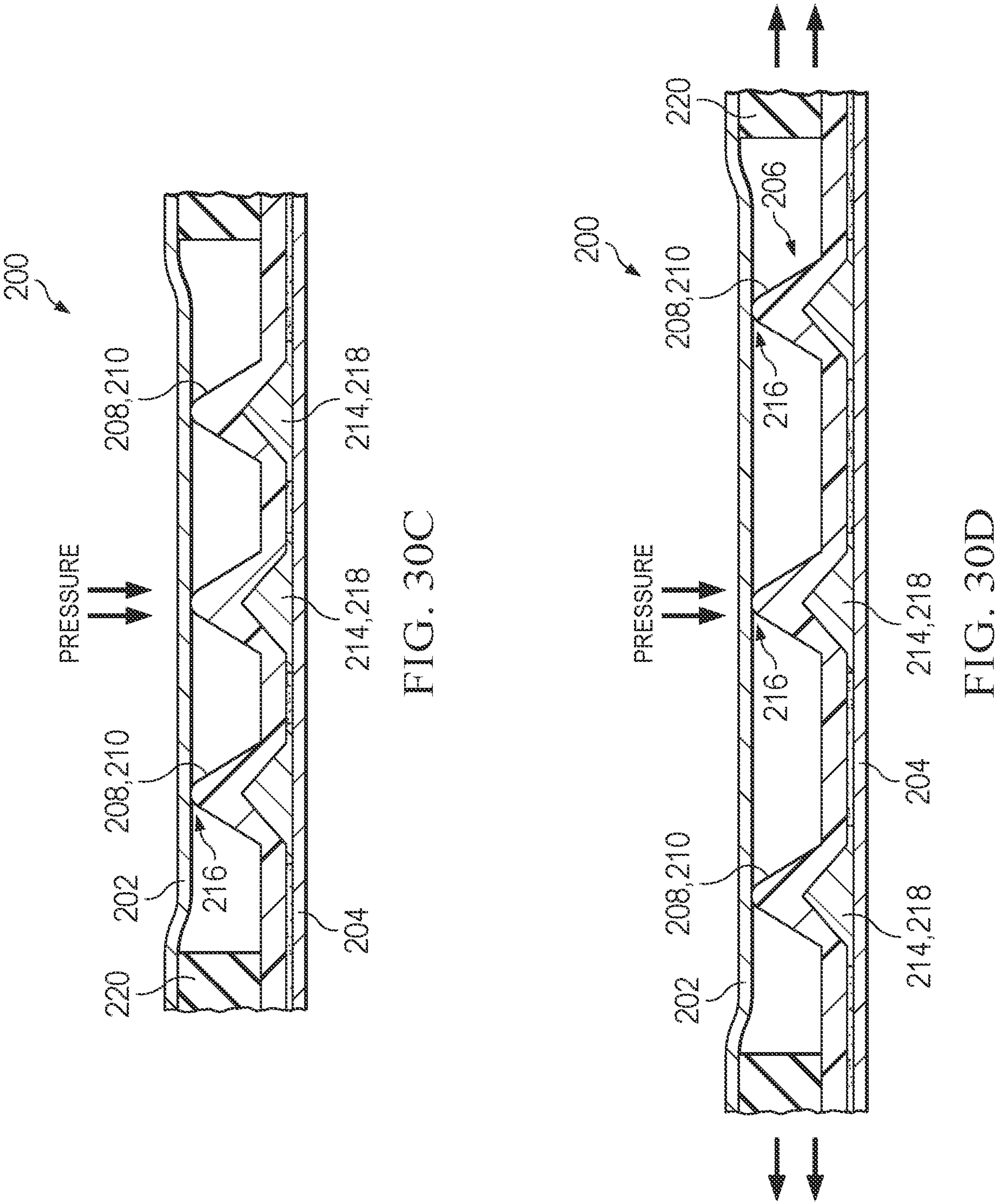

Referring to FIG. 30A, the resistive pressure sensor 200 comprises a stretchable top electrode 202, a stretchable bottom electrode 204, and an array 206 of peaked structures 208 between the stretchable top and bottom electrodes 202,204. Each peaked structure 208 has a tip 216 comprising an electrically conductive material and a base 218 comprising a stiffening material 214 and/or having a stiffening function. The tip 216 is in contact with the stretchable top electrode 202 and the base 218 is in contact with the stretchable bottom electrode 204. As with the capacitive sensor 100, the peaked structures 208 may have a pyramidal, conical, domed, or other three-dimensional shape having an apex that widens to a broader base, where the apex has a small radius of curvature (e.g., 0-30°) to ensure a small region of contact between the tips 216 of the peaked structures 208 and the stretchable top electrode 202. When a normal pressure is applied to the resistive pressure sensor 200, as shown in FIGS. 30C and 30D, the contact area between the tips 216 and the stretchable top electrode 202 increases. Accordingly, a change in resistance of the pressure sensor 200 may monotonically reflect the magnitude of the applied pressure. Advantageously, the resistance measured by the soft pressure sensor 200 is substantially invariant under in-plane stretching. A resistance that is "substantially invariant" (or "substantially unchanged") under in-plane stretching varies by about 2% or less on average while the pressure sensor 200 is undergoing in-plane stretching and/or bending.

The pressure sensor 200 includes one or more spacers 220 extending between the stretchable top electrode 202 and the stretchable bottom electrode 204 to help maintain the spacing of the top and bottom electrodes 202,204 under stretching deformation. Each of the one or more spacers 220 is positioned outside the array 206 of peaked structures 208. The resistive pressure sensor 200 can maintain a substantially unchanged contact area between the tips 216 of the peaked structures 208 and the stretchable top electrode 202 when under stretching deformation due at least in part to the stiffening material 214 that may be included at the base 218 of each of the peaked structures 208 and the presence of the one or more spacers 220. This can be seen by comparing the stretched sensors 200 of FIG. 30B and FIG. 30D with the unstretched sensors 200 of FIGS. 30A and 30C. With this design, in-plane strain applied to the resistive pressure sensor 200 leaves the peaked structures 208 virtually unaltered in geometry, which allows for the same resistance to be measured in response to normal pressures regardless of the strain state.

Each peaked structure 208 may include a stretchable conductive film 210 overlying the stiffening material 214 and defining the tip 216, where the stretchable conductive film 210 comprises the conductive material. The conductive material may comprise metal particles, carbon particles, a conductive polymer, and/or a conductive polymer composite. In some examples, the stretchable conductive film 210 may further comprise an elastomer, and the conductive material may be coated on the elastomer. The stiffening material 214 at the base 218 of the peaked structures 208 typically comprises a polymer having a stiffness or modulus of at least about 0.3 GPa, or at least about 1 GPa, or at least about 3 GPa. The stiffening material 214 may be conductive or substantially non-conductive. In some examples, the base 218 of each peaked structure 208 may provide stiffening due to its geometry, without the presence of a separate stiffening material 214. Also or alternatively, the base 218 may be in contact with and/or integrally formed with the stretchable bottom electrode 204, and each peaked structure 208 may or may not include the stretchable conductive film 210. For example, the stretchable bottom electrode 204 and the array 206 of peaked structures 208 may be integrally formed from an elastomer comprising the conductive material (e.g., a conductive elastomer). In such an example, both the tip 216 and the base 218 of each peaked structure 208 may comprise the conductive material.

The one or more spacers 220 may be positioned on opposing sides of the array 206. In some examples, the one or more spacers 220 may be positioned on all sides of the array. The spacers 220 may be discrete structures (e.g., shaped as pillars), or elongated or continuous structures (e.g., shaped as rods) that have a height comparable or identical to that of the peaked structures 208. When employed on opposing sides or on all sides of the array 106, the spacers 120 may comprise a plurality of the discrete or continuous structures that partly or completely surround the array 106. Alternatively, a single spacer 120 that extends around the perimeter so as to completely surround the array 106 may be suitable. The one or more spacers 120 may comprise an elastomer, such as a silicon elastomer, e.g., polydimethylsiloxane (PDMS).

Analogous to the design of the capacitive sensor 100, the stretchable top electrode 202 may comprise a first conductive layer on a first elastomeric layer, and the tip 216 of each peaked structure 208 may be in contact with the first conductive layer. The stretchable bottom electrode 204 may comprise a second conductive layer on a second elastomeric layer, and the base 218 of each peaked structure 208 may be in contact with the second conductive layer. The first and second conductive layers may comprise carbon and/or metal particles, and/or may be formed from a conductive particle/elastomer paste or a stretchable conductive polymer (e.g., conductive elastomer).

The soft resistive pressure sensor 200 may be used to measure or monitor pressure in an open- or closed-loop process. The resistive pressure sensor 200 may be attached to part or an appendage of a human body or soft robot. An object may be contacted with the soft pressure sensor, and a resistance of the soft pressure sensor may be measured, thereby obtaining touch information during the contacting. The object may be an inanimate object, an animal or a human being. The resistance measured by the soft pressure sensor may be transmitted to a closed loop controller, and a position of the part or appendage with respect to the object may be adjusted to achieve a predetermined resistance, and thus a preset pressure. Advantageously, as the soft pressure sensor is stretched or bent to accommodate motion of the part or appendage, the resistance measured by the soft pressure sensor may be substantially unchanged.

Experimental Methods

Materials

Stretchable Ag nanoparticle paste 126-49 was purchased from Creative Materials. Tetramethylammonium hydroxide (TMAH) solution (25 wt % in $H_2O$) and hexamethylenediamine (HMDA) were purchased from Sigma-Aldrich and used as received. 1-ethyl-3-methylimidazolium bis(trifluoromethylsulfonyl)imide (EMIM:TFSI) was purchased from TCI America and used as received. Both silicone adhesive and Ecoflex 00-10 were purchased from Smooth-on. Electrically conductive epoxy adhesive 8331 was purchased from MG Chemicals. Poly(vinylidene fluoride-co-hexafluoropropylene) (PVDF-HFP) 2299 was supplied by 3M Dyneon Fluoroelastomer and used as received. Polydimethylsiloxane (PDMS) Sylgard 184 was purchased from Dow Corning.

Fabrication of Strain-Insensitive Pressure Sensor

PVDF-HFP was dissolved in acetone with the weight ratio, in this example, of 1:6. The ionic liquid EMIM:TFSI was added into the mixture, in varied amounts with the weight ratios of 15%, 30% and 60%. The solution was stirred at room temperature for ~4 h. HMDA was dissolved in acetone with a concentration of 80 mg/mL and added into PVDF-HFP/EMIM:TFSI solution and stirred at 300 r.p.m for 10 min.

To create a silicon mold, a layer of photoresist (AZ 703) was spin-coated on a $Si/SiO_2$ wafer. After baking and exposure, the $Si/SiO_2$ wafer was patterned by reactive-ion etching to produce a square array of opened windows ($500\times500$ $\mu m^2$) with exposed Si. Next, an inverted pyramid array with a height of 350 μm was developed by wet etching with TMAH solution (5 wt. % in $H_2O$) at 80° C.

Then, the surface of the Si mold was modified by 02 plasma (400 W, 200 mTorr) to enhance its hydrophilicity. A sacrificial layer of Dextran (5 wt % in water) was spin-coated on the Si mold at 3000 r.p.m. for 30 s, followed by annealing at 80° C. for 10 minutes. PVDF-HFP/EMIM:TFSI/HMDA ionic gel was drop-cast onto the Si mold and then the ionic gel was cured at room temperature for 4 hours, to form a continuous layer of 160 μm in thickness. Subsequently, a polyimide mask was placed atop the continuous layer so that its pattern aligned with the pyramids. An electrically conductive epoxy adhesive was blade-coated across the masked continuous layer and on the bottom surface of the pyramids; the mask was removed, leaving a stiffening electrode at the base of each pyramid. After curing of the stiffening electrodes at 80° C. for 10 min, the sacrificial layer was dissolved, and the continuous layer was peeled off from the Si mold. PDMS film with a thickness of 350 μm was cut into the required dimension ($14\times4\times0.35$ $mm^3$) for the two spacers, and then bonded to the two short edges of the continuous layer, 2 mm away from the pyramid microstructure.

To construct the bottom and top electrode substrates, $Si/SiO_2$ wafers with Dextran sacrificial layers were coated with Ecoflex 00-10 (part A:part B=1:1) by spin-coating at 1500 r.p.m. for 30 s and at 3500 r.p.m. for 30 s, respectively. Next, a patterned polyimide mask was affixed to the elastomer-coated wafer and an Ag nanoparticle paste layer (~50 μm) was added by blade-coating, followed by curing at 150° C. for 30 min. Then, the electrode was peeled-off from the Si wafer by dissolving the sacrificial layer; the top electrode was completed at this point. For the bottom electrode only, another Ag nanoparticle paste layer, which may act as the adhesive layer, was added by blade-coating. After this, the dielectric layer with two spacers was placed on top of the adhesive layer to assemble the lower part (this includes the bottom electrode, adhesive layer and continuous layer) of the sensor. The lower part of the sensor was pre-cured at 80° C. for 1 hour and then post-cured at 150° C. for 5 min. Finally, the top electrode was bonded to the two spacers to complete the sensor.

Fabrication of Reference Sensors

For the fabrication of reference sensors, all steps and parameters are consistent with those of the inventive sensor, except the experimental variables. To fabricate a reference sensor without stiffening micro-electrodes, the dielectric layer was directly peeled off of the Si mold after curing, without blade-coating the stiffening micro-electrodes of electrically conductive epoxy adhesive. For a reference sensor without ionic liquid (0 wt. %), no ionic liquid was added into PVDF-HFP/HMDA solution. The reference sensor without spacers was fabricated by bonding two terminals of the top electrode directly to the edge of the pyramid structure. The adhesive layer was not blade-coated on the bottom electrode before assembling the dielectric layer to fabricate a reference sensor without the adhesive layer. PDMS substrate film and Ecoflex substrate films with different thicknesses were used to build reference sensors.

Ionic Elastomer and Electrode Characterization

To characterize the mechanical performance of PVDF-HFP/EMIM:TFSI/HMDA ionic elastomer films, the ionic gel was drop-casted onto glass slides and cured at room temperature for 12 hours to obtain sample sheets ($15\times4\times0.08$ $mm^3$). The mechanical testing was performed by a Zwick-Roell zwickiLine Z0.5 instrument. All the tensile experiments were performed at room temperature (25° C.) with a strain rate of 20 mm/min for both stretching and relaxing steps. The SEM images were taken by a FEI Quanta 650 SEM.

To characterize the capacitance of the EDL, ionic elastomer films were prepared with the dimension of $20\times30\times0.15$ $mm^3$. Then the films were sandwiched between two Ag nanoparticle paste electrodes with an area of $10\times10$ $mm^2$. The capacitance was measured with a Keysight E4980AL inductance capacitance and resistance (LCR) meter. For the testing of sheet resistance-strain of electrodes, an electrode was stretched to various strains with a customized stretcher and the resistance values were measured with a Keysight 6514 electrometer. To characterize the robustness of electrodes, an electrode was stretched to 50% for 500 times, during which the resistances were measured with the electrometer. The microscope images of ion gel films and electrodes were taken with a ZEISS microscope (Axioscope 5).

Device Characterization

All the capacitance responses were measured using the LCR meter (at 1 kHz frequency, oscillator voltage level of 1 V without d.c. bias). Pressures were applied by loading various weights onto the sensors. Cyclic stretching tests of the sensor were done by stretching the sensor to 50% strain for 500 times; the capacitance responses were measured at the 1st, 250th and 500 th cycles with a pressure of 4 kPa. Cyclic compression tests of the sensor were done by compressing the sensor 500 times with a cyclic pressure of 0.67 kPa under 0% and 50% strains; the capacitance response was recorded throughout the testing by a customized Labview program connected to the LCR meter. The response time was measured by quickly loading a pressure of 1 kPa on the sensor. To investigate the limit of detection of the sensor, a small piece of paper (0.2 Pa) was repeatedly loaded onto the sensor and the capacitance response was recorded.

Prosthetic and Soft-Robotic Applications

A pneumatically-actuated soft robotic hand was integrated with a motorized robotic arm. The capacitance of the sensor, which was attached to the fingertip, was measured by an LCR meter in the real time, and then was transmitted to the control circuit (Arduino) of robotic arm through the Labview program of the LCR meter. The movement of robotic arm is determined by the difference of targeted and current capacitances.

The subject-matter of the disclosure may also relate, among others, to the following aspects:

A first aspect relates to a soft pressure sensor comprising: a stretchable top electrode; a stretchable bottom electrode; an array of peaked structures between the stretchable top and bottom electrodes, the peaked structures being defined by protruding regions of a continuous film conformally overlying an array of stiffening electrodes on the stretchable bottom electrode, where a tip of each protruding region is in contact with the stretchable top electrode and a base of each stiffening electrode is in contact with the stretchable bottom electrode, and one or more spacers extending between and bonded to the stretchable top electrode and the continuous film on the stretchable bottom electrode, each of the one or more spacers being positioned outside the array of peaked structures, wherein a capacitance measured by the soft pressure sensor is substantially invariant under in-plane stretching.

A second aspect relates to the soft pressure sensor of the first aspect, wherein the peaked structures have a pyramidal, dome-shaped, conical, or another deformable shape.

A third aspect relates to the soft pressure sensor of any preceding aspect, wherein the capacitance is an electric double layer (EDL) capacitance.

A fourth aspect relates to the soft pressure sensor of any preceding aspect, wherein the continuous film comprises an ionically conductive elastomer or ion gel.

A fifth aspect relates to the soft pressure sensor of the fourth aspect, wherein the stretchable top electrode comprises a first conductive layer on a first elastomeric layer, and the tip of each protruding region is in contact with the first conductive layer, and wherein the stretchable bottom electrode comprises a second conductive layer on a second elastomeric layer, and the base of each stiffening electrode is in contact with the second conductive layer.

A sixth aspect relates to the soft pressure sensor of the fourth or the fifth aspect, wherein the ionically conductive elastomer or ion gel is prepared from an ionic liquid, an elastomer, and an optional crosslinker.

A seventh aspect relates to the soft pressure sensor of the sixth aspect, wherein the ionic liquid comprises 1-ethyl-3-methylimidazolium bis(trifluoromethylsulfonyl)imide (EMIM:TFSI), the elastomer comprises poly(vinylidene fluoride-co-hexafluoropropylene) (PVDF-HFP), and the optional crosslinker comprises hexamethylenediamine (HMDA).

An eighth aspect relates to the method of any one of the fifth through the seventh aspects, wherein the first and second conductive layers comprise carbon and/or metal particles, and/or are formed from a conductive particle/elastomer paste or a stretchable conducting polymer.

A ninth aspect relates to the soft pressure sensor of any preceding aspect, wherein the one or more spacers are positioned on opposing sides of the array.

A tenth aspect relates to the soft pressure sensor of any preceding aspect, wherein the one or more spacers are positioned on all sides of the array.

An eleventh aspect relates to the soft pressure sensor of any preceding aspect, wherein the one or more spacers comprise an elastomer.

A twelfth aspect relates to the soft pressure sensor of any preceding aspect, wherein the stiffening electrodes have a stiffness of at least about 0.3 GPa.

A thirteenth aspect relates to the soft pressure sensor of any preceding aspect, wherein the stiffening electrodes comprise conductive and adhesive materials.

A fourteenth aspect relates to the soft pressure sensor of any preceding aspect, further comprising an electrically conductive adhesive between the continuous film and the stretchable bottom electrode.

A fifteenth aspect relates to the soft pressure sensor of any preceding aspect, wherein the array comprises a one- or two-dimensional array including from 2 to 200 peaked structures.

A sixteenth aspect relates to the soft pressure sensor of any preceding aspect exhibiting a pressure sensitivity of at least about 2 $kPa^{-1}$ and/or a strain insensitivity of at least about 98% up to 50% strain.

A seventeenth aspect relates to a method of measuring or monitoring pressure, the method comprising: attaching the soft pressure sensor of any preceding aspect to a part or an appendage of a human body or soft robot; contacting an object with the soft pressure sensor; and measuring a capacitance of the soft pressure sensor, thereby obtaining touch information during the contacting.

An eighteenth aspect relates to the method of the seventeenth aspect, further comprising transmitting the capacitance measured by the soft pressure sensor to a closed loop controller; and adjusting a position of the part or appendage with respect to the object to achieve a predetermined capacitance and thus a preset pressure.

A nineteenth aspect relates to the seventeenth or eighteenth aspect, wherein, as the soft pressure sensor is stretched or bent to accommodate motion of the part or appendage, the capacitance measured by the soft pressure sensor is substantially unchanged.

A twentieth aspect relates to any one of the seventeenth through the nineteenth aspects, wherein the capacitance is an electric double layer (EDL) capacitance.

A twenty-first aspect relates to a soft pressure sensor comprising: a stretchable top electrode; a stretchable bottom electrode; an array of peaked structures between the stretchable top and bottom electrodes, each peaked structure having a tip comprising a conductive material and a base comprising a stiffening material and/or having a stiffening function, the tip being in contact with the stretchable top electrode and the base being in contact and/or integrally formed with the stretchable bottom electrode; and one or more spacers extending between the stretchable top electrode and the stretchable bottom electrode, each of the one or more spacers being positioned outside the array of peaked structures, wherein a resistance measured by the soft pressure sensor is substantially invariant under in-plane stretching.

A twenty-second aspect relates to the soft pressure sensor of the twenty-first aspect, wherein each peaked structure includes a stretchable conductive film overlying the stiffening material/structure and defining the tip, the stretchable conductive film comprising the conductive material.

A twenty-third aspect relates to the soft pressure sensor of the twenty-first or twenty-second aspect, wherein the stretchable conductive film further comprises an elastomer, and wherein the conductive material is coated on the elastomer.

A twenty-fourth aspect relates to the soft pressure sensor of any one of the twenty-first through the twenty-third aspects, wherein the conductive material comprises metal particles, carbon particles, a conductive polymer, and/or a conductive polymer composite.

A twenty-fifth aspect relates to the soft pressure sensor of any one of the twenty-first through the twenty-fourth aspects, wherein the stiffening material comprises a polymer having a stiffness or modulus of at least about 0.3 GPa.

A twenty-sixth aspect relates to the soft pressure sensor of any one of the twenty-first through the twenty-fifth aspects, wherein the stretchable top electrode comprises a first conductive layer on a first elastomeric layer, and the tip of each peaked structure is in contact with the first conductive layer, and wherein the stretchable bottom electrode comprises a second conductive layer on a second elastomeric layer, and the conductive material is in contact with the second conductive layer.

A twenty-seventh aspect relates to the soft pressure sensor of the twenty-sixth aspect, wherein the first and second conductive layers comprise carbon and/or metal particles, and/or are formed from a stretchable conductive particle/elastomer paste or a stretchable conductive polymer.

A twenty-eighth aspect relates to the soft pressure sensor of any one of the twenty-first through the twenty-seventh aspects, wherein the one or more spacers are positioned on opposing sides of the array.

A twenty-ninth aspect relates to the soft pressure sensor of any one of the twenty-first through the twenty-eighth aspects, wherein the one or more spacers are positioned on all sides of the array.

A thirtieth aspect relates to the soft pressure sensor of any one of the twenty-first through the twenty-ninth aspects, wherein the one or more spacers comprise an elastomer.

A thirty-first aspect relates to a method of measuring or monitoring pressure, the method comprising: attaching the soft pressure sensor of any one of the twenty-first through the thirtieth aspects to a part or an appendage of a human body or soft robot; contacting an object with the soft pressure sensor; measuring a resistance of the soft pressure sensor, thereby obtaining touch information during the contacting.

A thirty-second aspect relates to the method of the thirty-first aspect, further comprising transmitting the resistance measured by the soft pressure sensor to a closed loop controller; and adjusting a position of the part or appendage with respect to the object to achieve a predetermined resistance and thus a preset pressure.

A thirty-third aspect relates to the method of the thirty-first or the thirty-second aspect, wherein, as the soft pressure sensor is stretched or bent to accommodate motion of the part or appendage, the resistance measured by the soft pressure sensor is substantially unchanged.

To clarify the use of and to hereby provide notice to the public, the phrases "at least one of <A>, <B>, . . . and <N>" or "at least one of <A>, <B>, <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed. Unless otherwise indicated or the context suggests otherwise, as used herein, "a" or "an" means "at least one" or "one or more."

While various embodiments have been described, it will be apparent to those of ordinary skill in the art that many more embodiments and implementations are possible. Accordingly, the embodiments described herein are examples, not the only possible embodiments and implementations.

What is claimed is:

1. A soft pressure sensor comprising:

a stretchable top electrode comprising a first elastomeric layer;

a stretchable bottom electrode comprising a second elastomeric layer;

an array of peaked structures between the stretchable top and bottom electrodes, the peaked structures comprising an array of stiffening electrodes on the stretchable bottom electrode and a continuous film conformally overlying the array of stiffening electrodes, the continuous film conforming to a shape of each of the stiffening electrodes such that protruding regions are formed in the continuous film, where a tip of each protruding region is in contact with the stretchable top electrode and a base of each stiffening electrode is in contact with the stretchable bottom electrode, and one or more spacers extending between and bonded to the stretchable top electrode and the continuous film on the stretchable bottom electrode, each of the one or more spacers being positioned outside the array of peaked structures, wherein a capacitance measured by the soft pressure sensor is substantially invariant under in-plane stretching.

2. The soft pressure sensor of claim 1, wherein the peaked structures have a pyramidal, dome-shaped, conical, or another deformable shape.

3. The soft pressure sensor of claim 1, wherein the continuous film comprises an ionically conductive elastomer or ion gel.

4. The soft pressure sensor of claim 3, wherein the stretchable top electrode comprises a first conductive layer on the first elastomeric layer, and the tip of each protruding region is in contact with the first conductive layer, and wherein the stretchable bottom electrode comprises a second conductive layer on the second elastomeric layer, and the base of each stiffening electrode is in contact with the second conductive layer.

5. The soft pressure sensor of claim 1, wherein the one or more spacers comprise an elastomer.

6. The soft pressure sensor of claim 1, wherein the stiffening electrodes have a stiffness of at least about 0.3 GPa.

7. The soft pressure sensor of claim 1, exhibiting a pressure sensitivity of at least about 2 kPa-1 and/or a strain insensitivity of at least about 98% up to 50% strain.

8. The method of claim 1, wherein the capacitance is an electric double layer (EDL) capacitance.

9. The soft pressure sensor of claim 1, wherein the tip has a radius of curvature in a range from 0-30° to ensure a small region of contact between the protruding regions and the stretchable top electrode.

10. The soft pressure sensor of claim 1, wherein the stiffening electrodes have a stiffness of at least about 1 GPa.

11. The soft pressure sensor of claim 1, further comprising an electrically conductive adhesive between the continuous film and the stretchable bottom electrode in regions between the stiffening electrodes.

12. A method of measuring or monitoring pressure, the method comprising:

attaching the soft pressure sensor of claim 1 to a part or an appendage of a human body or soft robot;

contacting an object with the soft pressure sensor;

measuring a capacitance of the soft pressure sensor, thereby obtaining touch information during the contacting.

13. The method of claim 12, further comprising transmitting the capacitance measured by the soft pressure sensor to a closed loop controller; and adjusting a position of the part or appendage with respect to the object to achieve a predetermined capacitance and thus a preset pressure.

14. The method of claim 12, wherein, as the soft pressure sensor is stretched or bent to accommodate motion of the part or appendage, the capacitance measured by the soft pressure sensor is substantially unchanged.

* * * * *